United States Patent [19]
Meyers et al.

[11] Patent Number: 5,925,064
[45] Date of Patent: Jul. 20, 1999

[54] FINGERTIP-MOUNTED MINIMALLY INVASIVE SURGICAL INSTRUMENTS AND METHODS OF USE

[75] Inventors: William C. Meyers, Worcester; Steven Ek, Bolton, both of Mass.; Javier Verdura, Marietta, Ga.; Maureen E. Carroll, Atlanta, Ga.; Kirk W. Charles, Austell, Ga.

[73] Assignees: University of Massachusetts, Boston; Smith & Nephew, Inc., Andover, both of Mass.

[21] Appl. No.: 08/777,665

[22] Filed: Dec. 31, 1996

Related U.S. Application Data

[60] Provisional application No. 60/017,854, Jul. 1, 1996.
[51] Int. Cl.$^6$ ...................................................... A61B 17/28
[52] U.S. Cl. ............................................................. 606/205
[58] Field of Search .................................. 606/52, 53, 1, 606/170, 174, 180, 205–211

[56] References Cited

U.S. PATENT DOCUMENTS

| | | | |
|---|---|---|---|
| 2,846,766 | 8/1958 | Harter | 606/174 |
| 3,834,021 | 9/1974 | White et al. | 606/174 |
| 4,726,371 | 2/1988 | Gibbens | 606/174 |
| 5,079,629 | 1/1992 | Oz . | |
| 5,176,696 | 1/1993 | Saunders . | |
| 5,312,423 | 5/1994 | Rosenbluth et al. . | |
| 5,356,424 | 10/1994 | Buzerak et al. . | |
| 5,383,875 | 1/1995 | Bays et al. . | |
| 5,423,795 | 6/1995 | Eckert et al. . | |
| 5,441,059 | 8/1995 | Dannan . | |
| 5,441,486 | 8/1995 | Yoon . | |
| 5,456,684 | 10/1995 | Schmidt et al. . | |
| 5,501,698 | 3/1996 | Roth et al. . | |

FOREIGN PATENT DOCUMENTS

| | | |
|---|---|---|
| 0 106 748 | 4/1984 | European Pat. Off. . |
| WO 95/13023 | 5/1995 | WIPO . |
| WO 95/22289 | 8/1995 | WIPO . |
| WO 96/27991 | 9/1996 | WIPO . |

OTHER PUBLICATIONS

Cohn et al., "Surgical Applications of Milli–Robots," *J. Robotic Systems*, 12(6):401–416, 1995.
Goldsmith, "Future Surgery: Minimal Invasion," *Med. News & Perspectives*, 264(21):2723, 1990.
Gorey et al., "Video–assisted Nissen's fundoplication using a hand–access port," *Min. Invas. Ther. & Allied Technol.*, 5:364–368, 1996.
"Mini surgical camera developed in Israel," *Clinica*, 659:18, 1995.
Sastry et al., "Medical Robotics," Web site page: http://robotics/eecs.berkeley.edu/~lara/medical.html, Jun. 12, 1996.

*Primary Examiner*—Michael Buiz
*Assistant Examiner*—William Lewis
*Attorney, Agent, or Firm*—Fish & Richardson P.C.

[57] ABSTRACT

The invention is a series of minimally invasive, miniature surgical instruments mounted directly on a surgeon's fingertips in a way that the surgeon can insert his or her hand into a patient through a minimal incision to perform surgical procedures, and also to use his or her fingers to manipulate tissues. The invention enables the surgeon to perform the procedures with all the benefits of minimally invasive surgery, but with much greater tactile sense, control, and ease of manipulation, than enabled by known minimally invasive surgical instruments.

30 Claims, 14 Drawing Sheets

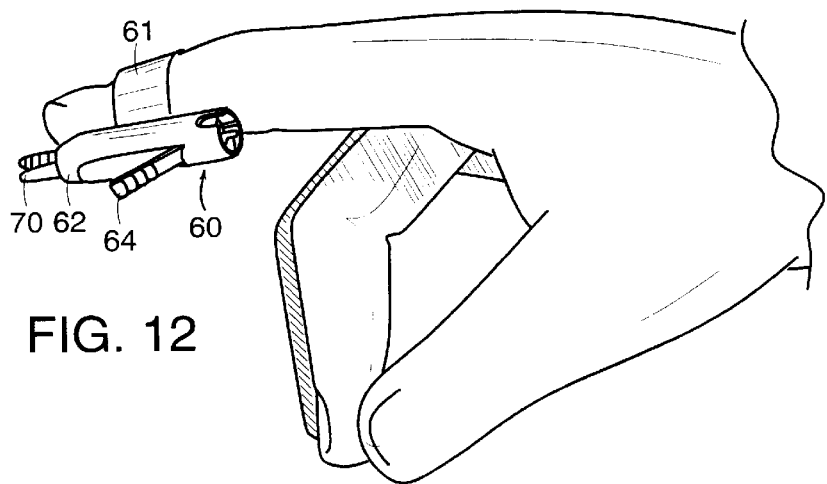
FIG. 12
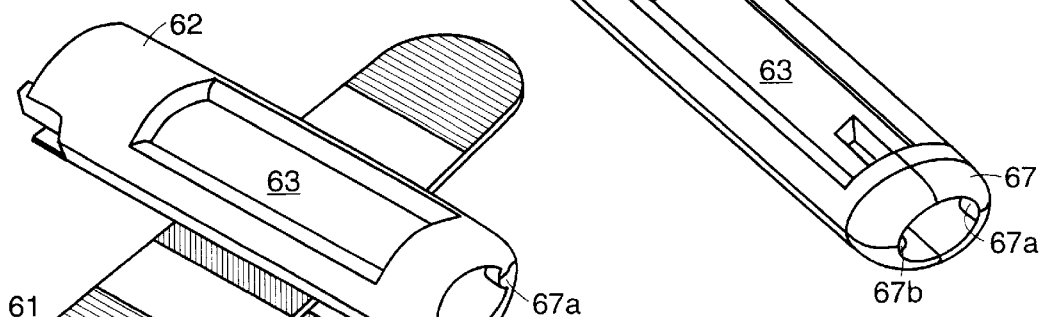
FIG. 13A
FIG. 13B
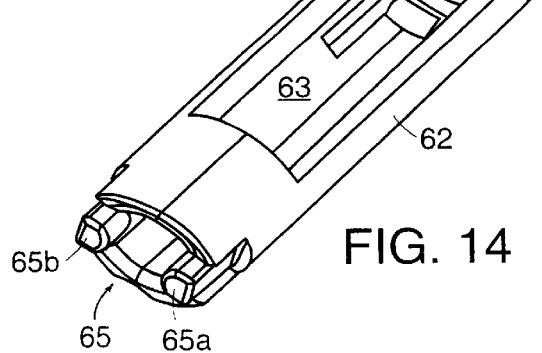
FIG. 14

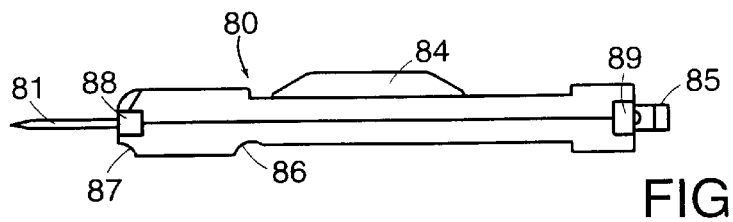
FIG. 30
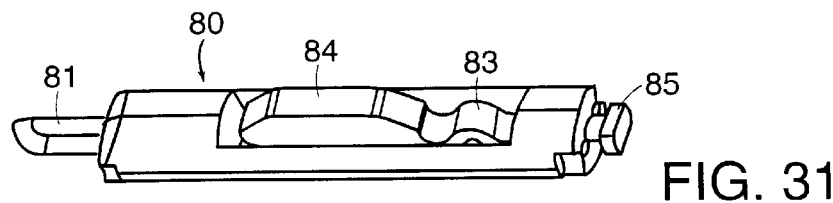
FIG. 31
FIG. 32A
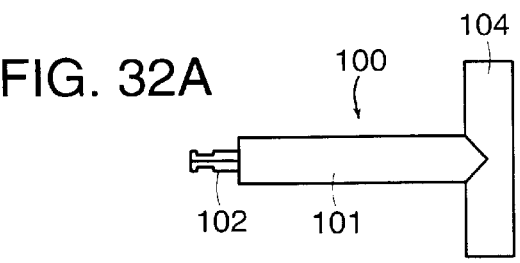
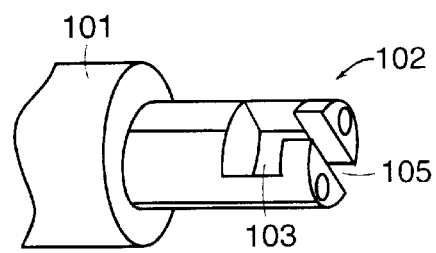
FIG. 32B
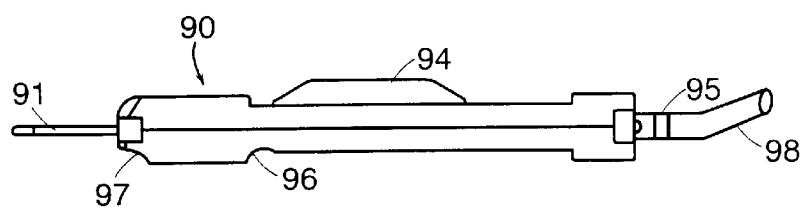
FIG. 33
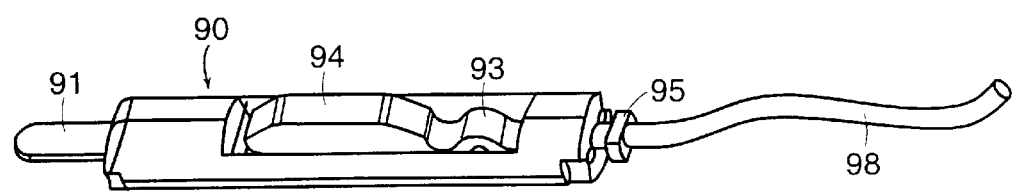
FIG. 34

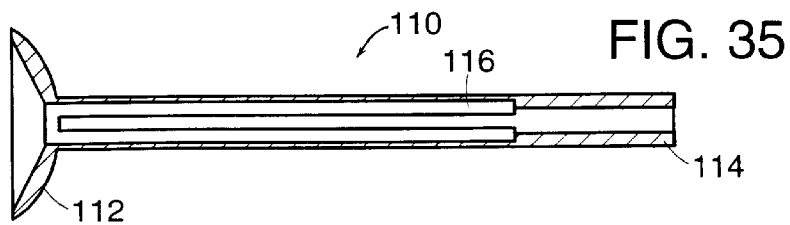
FIG. 35
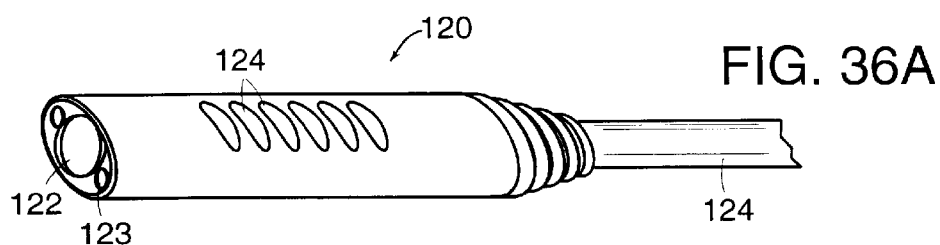
FIG. 36A
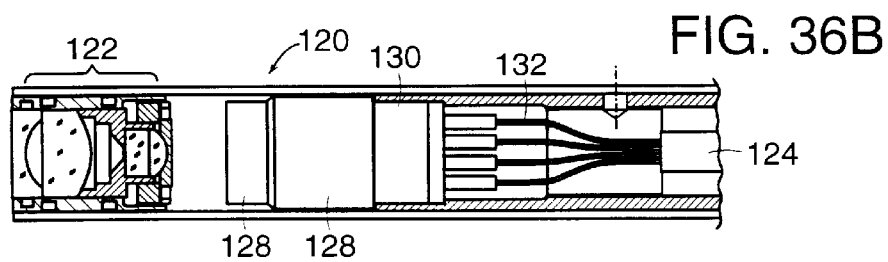
FIG. 36B
FIG. 37A
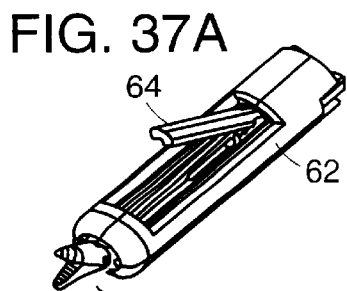
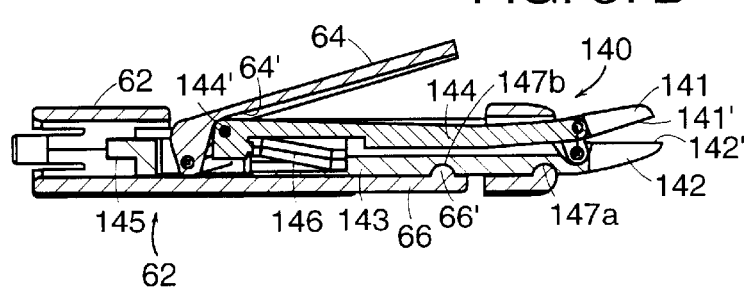
FIG. 37B

FINGERTIP-MOUNTED MINIMALLY INVASIVE SURGICAL INSTRUMENTS AND METHODS OF USE

CROSS REFERENCE TO RELATED APPLICATION

This application claims benefit of U.S. Provisional Application Ser. No. 60/017,854, filed Jul. 1, 1996.

BACKGROUND OF THE INVENTION

The invention relates to minimally invasive surgical instruments.

Minimally invasive surgical techniques, including endoscopic (gastrointestinal) and laparoscopic (abdominal) procedures, employ surgical instruments that are inserted into the body through a pre-existing orifice or a small puncture or incision rather than the larger incision used in traditional, "open" surgery. Minimally invasive procedures have several advantages over open surgery, the main one being minimization of trauma to healthy tissue. As a result, recovery is accelerated and the risk of complications from infection and scar adhesion is reduced. These considerations have motivated the application of minimally invasive techniques wherever feasible. However, the instruments used in these minimally invasive procedures impair or reduce surgical access, dexterity, efficiency, and in some cases safety, when compared to the use of standard instruments in open surgery.

Nearly all minimally invasive procedures employ means for imaging the surgical site in real time. These may be non-invasive, e.g., fluoroscopy, or invasive, using, for example, an optical fiberscope. Such "scopes" can be flexible, like the endoscope, which is employed in the gastrointestinal tract, or, when the operative site is sufficiently accessible, rigid, like the laparoscope, which is used in abdominal surgery. In both endoscopy and laparoscopy, viewing light is delivered to the surgical site by fiber optics, and the surgeon views the site on an external CRT.

Laparoscopic surgery takes place in an approximately 20×20×20 cm workspace inside the patient created by insufflating the abdominal cavity with air or a gas such as carbon dioxide. The laparoscope and laparoscopic instruments are inserted into the body through a 5 to 12 mm diameter cannulae inserted through one or more puncture incisions in the abdominal wall. There are many instruments available for use in laparoscopic procedures including biopsy forceps, various types of graspers, scissors, electrocautery devices, staplers, clip appliers, needle holders, and suture loops for ligation.

In spite of the benefits, there are several limitations of the laparoscopic instruments that make laparoscopy more awkward for the surgeon than traditional, open surgery, and the nature of the instruments require a long learning curve for a surgeon to become proficient in their use. Even after learning how to use these instruments properly, surgeons still lack a certain amount of dexterity, which makes some tasks, such as suturing and knot-tying inside the body cavity, difficult.

Based on the known disadvantages, attempts have been made to improve the position, tactile, and force senses perceived by the surgeon using these laparoscopic instruments in minimally invasive procedures. Force feedback assists in suture and knot tensioning and protects against inadvertent laceration of tissue outside of the field of view of the scope. Tactile sensing is useful for manipulating suture material or other objects held with the instruments, localizing small anatomical features such as subsurface blood vessels, and detecting features that are obscured from the video camera.

Efforts at implementing tactile feedback with these instruments have focused on elaborate linkage designs or the use of complex strain sensor arrays on the tip of the instrument coupled to stimulator arrays worn on the surgeon's fingertips, e.g., on a glove, at a point remote from the tip of the instrument. Such systems have had some experimental success, but are complicated, both to design and to manufacture.

SUMMARY OF THE INVENTION

The invention is based on the discovery that a tiny surgical instrument can be mounted directly on a surgeon's fingertip in a way that the surgeon can insert his or her hand into the patient through a minimal incision to perform surgical procedures, and also to use his or her fingers to manipulate tissues. The invention enables the surgeon to perform the procedures with all the benefits of minimally invasive surgery, but with much greater tactile sense, control, and ease of manipulation, than enabled by known minimally invasive surgical instruments.

In general, the invention features a fingertip-mounted minimally invasive surgical instrument including a mount, e.g., a harness or tool cartridge holder, to secure the instrument to a fingertip (e.g., by a web or strap); a retracting/deploying mechanism operably connected to the harness or a tool cartridge connected to a holder; and a tool connected directly to the retracting/deploying mechanism or to the tool cartridge, wherein the retracting/deploying mechanism is arranged to permit the tool or the entire tool cartridge to be moved into a retracted position relative to the mount (e.g., harness or holder) to expose the fingertip, and into a deployed position relative to the mount for use of the tool. The instrument can further include an attachment mechanism that rotatably connects the harness to the retracting/deploying mechanism.

For example, the attachment mechanism can include an attachment stud and a compression member arranged to secure the retracting/deploying mechanism to the harness and to enable the retracting/deploying mechanism to rotate from a deployed position to a retracted position. The harness can include a convex outer surface that mates with a concave surface of the retracting/deploying mechanism.

The instrument can further include a spring arranged to bias the moving jaw in an open position with respect to the stationary jaw. In addition, a portion of the retracting/deploying mechanism, tool cartridge, or holder can be hollowed out to house the actuator when the tool is in a closed position.

In another embodiment, the mount, e.g., harness or tool cartridge holder, can include openings for insertion of a strap to secure the harness to a finger. In other embodiments, the mount can include "wings" of tape or a strap of hook and loop material that can be used to secure the mount to a finger. These tapes or straps can be fixed to the mount by welding or glue.

In another aspect, the invention features a method of performing a minimally invasive surgical procedure in a patient by creating in the patient an incision sized to fit a hand; securing an instrument of the invention to a fingertip of the hand; inserting the hand including the instrument into the patient; and performing the surgical procedure using the instrument. The method can further include securing an additional instrument onto another of the fingers prior to inserting the hand into the patient.

In the method, the tool of the instrument can be moved into a deployed position prior to performing the surgical procedure, and into a retracted position after performing the surgical procedure, without removing the hand from within the patient. For example, the tool of the instrument can be moved into a retracted position to enable the finger to be used to manipulate tissue in the patient, without removing the hand from within the patient.

In another aspect, the invention features a fingertip-mounted minimally invasive surgical instrument assembly. The assembly includes a tool cartridge holder for securing the instrument to a fingertip, e.g., by an adhesive band, and an elongate tool cartridge including a frame and a tool connected to a distal end of the frame, wherein the frame is configured to be movably attached to the holder, and the frame and holder are configured such that the frame and the attached tool can move between a retracted position and a deployed position relative to the holder. For example, the holder can have a hollow, cylindrical housing where the tool cartridge is attached to the holder by being inserted into the housing. In this embodiment, the tool is sheathed within the housing when the tool cartridge is moved into a retracted position, and extends outside of the housing when the tool cartridge is moved into a deployed position.

In preferred embodiments, the holder includes a detent that engages a first notch on the tool cartridge frame to provide a locked, deployed position. The tool cartridge frame can include a second notch to engage the detent to provide a locked, retracted position. In certain embodiments, the tool or tool cartridge can include a stationary jaw, and a moving jaw connected to an actuator, and the tool can be a grasper, scissors, a scalpel, a clip applier, a needle holder, a miniature camera, e.g., a charge-coupled device (CCD) camera, or an electrocautery blade. In one embodiment, the actuator has a curved cross-section, and is curved along its longitudinal axis. In another embodiment, the actuator used in the tool cartridge is straight, and is moved about a pivot point, or imaginary pivot point, set as far proximal to the tool as possible within the tool cartridge.

In addition, the holder can include stops or tabs at one or both of the distal and proximal ends of the holder to temporarily prevent the tool cartridge from being removed from the holder absent manipulation by the surgeon.

In certain embodiments, the tool cartridge further includes a retracting/deploying mechanism, and the holder includes an opening to provide access to the retracting/deploying mechanism.

In another embodiment, the assembly can further include an extractor tool configured to engage an extractor tool interface on a proximal end of the tool cartridge frame. The assembly can also include a protective sleeve that includes an elongate, hollow cylinder configured to contact the holder and allow the tool cartridge to be removed with the extractor tool through the lumen of the sleeve.

In addition, the instrument or assembly can be fitted with fluid aspiration or irrigation conduits, or with electrical wiring, in which case the instrument can be used to perform aspiration or irrigation, or electrocautery of tissue in the patient.

The invention provides several advantages. One important advantage of the invention is that it enables the surgeon to perform hand-assisted minimally invasive surgery which provides the surgeon with tactile feedback that is lost when using known minimally invasive laparoscopic or endoscopic surgical instruments. Standard minimally invasive surgery instruments have one or more mechanical linkages that separate the surgeon's hand from the tool, e.g., resector, at the distal (patient) end of the instrument by a long tube or shaft and a handle. The compression and elongation of materials used in instruments in this configuration prevent a linear relationship between the surgeon's hand movements and the tool's movements. This, in turn, causes positional uncertainty, disrupts the surgeon's tactile sense of how much pressure is being exerted by the tool, and impairs the surgeon's ability to perform dissections or delicate resections of tissue.

Another advantage of the invention is that the instruments are mounted directly on the surgeon's fingertips in a retractable manner, and a different instrument can be mounted on each of the surgeon's fingertips. Alternatively, when using the tool cartridge and holder assembly, the surgeon can mount a single holder on a finger in a position that is most comfortable, e.g., either on the top, bottom, or side of his or her finger, and use only one holder. Either arrangement allows the surgeon to operate by hand within a cavity in the patient, and can avoid the need for repeated insertion and removal of the surgeon's hand through the wound either to remove the instrument to allow the surgeon to manipulate tissues with his fingers, or to exchange instruments. For example, the tool cartridges can be exchanged through a standard cannula using a long extractor tool, and a magazine of different tool cartridges.

Avoiding repeated insertions of the surgeon's hand causes less trauma to the patient, shortens the surgical procedure, and prevents the escape of insufflation gas from the patient's cavity. Further, the instruments' fingertip design, which allows the surgeon to bend all or most of the joints of his or her finger, provides the surgeon with maximum mobility.

In addition, the instruments are designed so that when the instrument is in a retracted position, the tool tip of the instrument is locked in a closed, safe position. This design prevents any accidental cutting or injuring of tissue when the surgeon uses his or her fingers to manipulate tissues, and when the surgeon inserts or removes his or her hand from a cavity within the patient.

Further, the new instruments are simple in design, can be easily manufactured, and can be manufactured to be disposable or sterilizable and reusable, as desired.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 12 is a schematic diagram of a tool cartridge and holder assembly mounted to a fingertip by means of a band or strap.

FIGS. 13A, 13B, and 14 are isometric schematic views of a tool cartridge holder.

FIG. 17 is a cross-sectional view along line 17—17 in FIG. 16.

FIG. 26B shows an alternative embodiment of the actuator.

FIG. 30 is a side schematic view of a scalpel cartridge.

FIG. 31 is an isometric schematic view of a scalpel cartridge.

FIGS. 32A and 32B are schematic views of an extractor tool for removing tool cartridges from holders.

FIG. 33 is a side schematic view of a spoon blade electrocautery cartridge.

FIG. 34 is an isometric schematic view of the spoon blade electrocautery cartridge of FIG. 33.

FIG. 35 is a cross-sectional view of an extractor tool sleeve.

FIGS. 36A and 36B are isometric and cross-sectional views, respectively, of a miniature camera tool cartridge.

FIGS. 37A and 37B are isometric and cross-sectional views, respectively, of a scissors tool cartridge in a holder.

DETAILED DESCRIPTION

Figure 1:
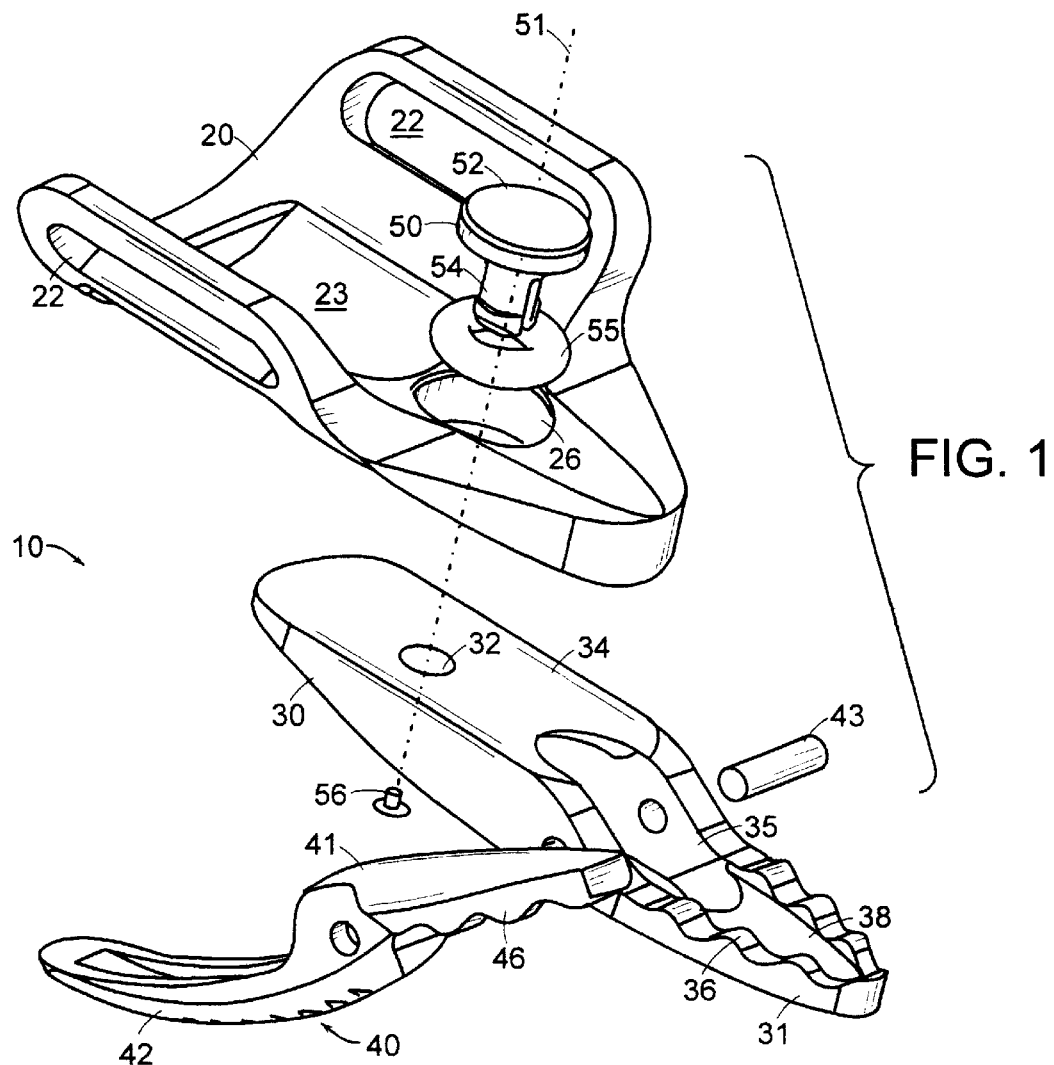
FIG. 1 is an exploded, isometric schematic view of a fingertip-mounted minimally invasive surgical grasper.

The instruments and methods of the invention enable a surgeon to perform hand-assisted surgical procedures with his or her hand inside a patient's body cavity with all the benefits of minimally invasive surgery, but with the tactile feedback, control, and ease of manipulation of traditional, open surgery. In addition, the new instruments can be used in open surgery as well, since they can provide greater feedback and control than their traditional surgical instrument counterparts.

The instruments allow the surgeon to regain tactile feedback because, being mounted directly on the surgeon's fingertips, they require minimal actuation or linkage mechanisms. Further, by having the instruments designed and mounted in such a way that the surgeon can manipulate them into a deployed or a retracted position with his or her thumb, the surgeon can easily use his or her fingertips to manipulate tissues. This ability to manipulate tissues without obstruction by the instruments is enhanced by the instruments' overall low profile design.

Fingertip-Mounted Minimally Invasive Surgical Instruments

In general, any surgical tool or tip normally found on traditional surgical instruments or on laparoscopic or endoscopic instruments can be adapted for use in the present invention. For example, graspers, needle holders, clip appliers, dissectors, resectors, scalpels, scissors, and basket punches can be incorporated into the instruments of the invention. In addition, fittings for a variety of tubes or conduits, e.g., for irrigation and aspiration, and for electrical wiring, e.g., for monopolar or bipolar electrosurgical applications, can be added to the instruments of the invention.

The tools are secured to the surgeon's finger via a mount that is firmly attached to the finger or to a glove worn over the finger. The mount can take several different forms. For example, the mount can be a harness that is permanently connected to a particular tool, or the mount can be a separate generic holder that accepts multiple different tool cartridges.

Each harness-mounted instrument includes several main components: (1) a harness that is used to mount the instrument to the surgeon's fingertip; (2) a tool, such as a grasper or scalpel; and (3) a retracting/deploying mechanism attached to the tool that allows the tool to be manipulated into either a deployed position for surgery, or a retracted, locked position for fingertip manipulation of tissues. The retracting/deploying mechanism is attached to the harness, e.g., by an attachment mechanism, or is designed as a part of the harness. In certain embodiments, a portion of the tool may be an integral part of the retracting/deploying mechanism when the tool has two operating surfaces, e.g., as in a grasper or scissors.

Each of the tool cartridge and holder assemblies also include several main components: (1) a generic tool cartridge holder that is used to mount interchangeable tool cartridges to the surgeon's fingertip; (2) a tool cartridge including a tool, such as a grasper or scalpel; and (3) a retracting/deploying mechanism attached to the tool cartridge that allows the tool to be manipulated into either a deployed position for surgery, or a retracted, locked position for fingertip manipulation of tissues. The retracting/deploying mechanism is attached to the cartridge which slides laterally within the holder. In certain embodiments, a portion of the tool may be an integral part of the frame of the tool cartridge, for example, when the tool has two operating surfaces, e.g., as in a grasper or scissors.

Figure 5:
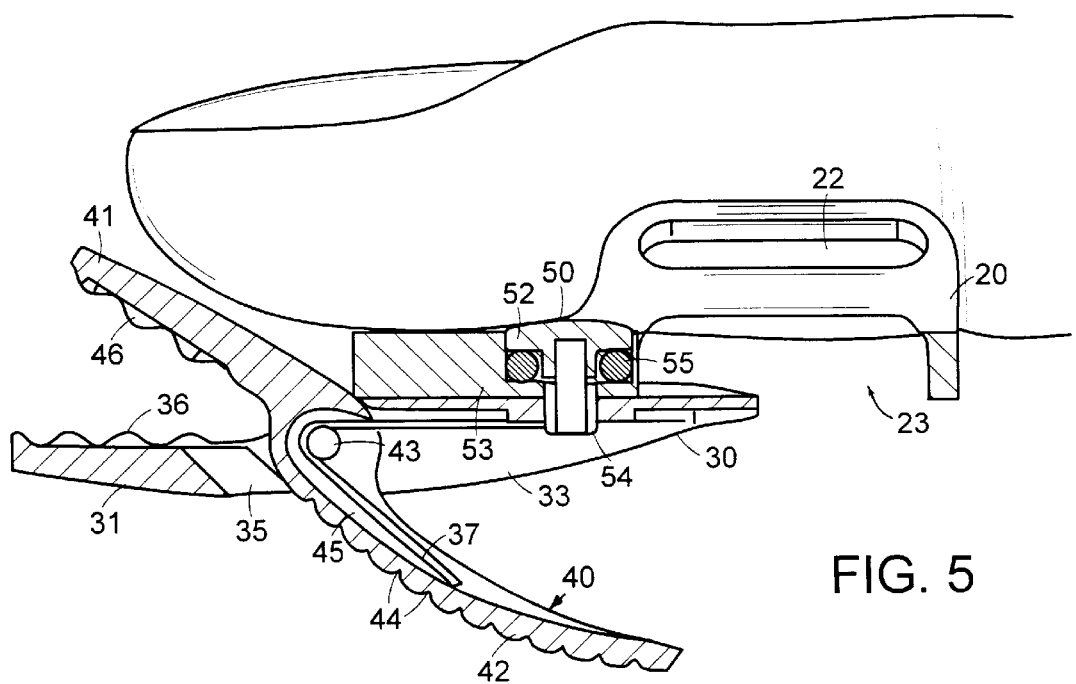
FIG. 5 is a cross-section side view of the surgical grasper of FIG. 2 sectioned along lines 5—5 in FIG. 4, and mounted on a fingertip.

All of the instruments also share certain features. For example, they all have a low overall profile, especially in the closed, retracted position, and are designed to fit on the fingertip above the first joint (as shown in FIG. 5), or the second joint (as shown in FIG. 12). In certain embodiments, e.g., where the mount is a harness, the retracting/deploying mechanism can be designed to rotate or swivel the tool from the deployed to the retracted position. This design allows for maximal extension of the tool beyond the harness in the deployed position while preserving the maximum mobility of the fingertip when the instrument is in the retracted position. In other embodiments, e.g., where the mount is a holder, the retracting/deploying mechanism can be configured to slide the tool from the deployed to the retracted position in parallel to the holder (or harness).

In all instruments, the retracting/deploying mechanism is also designed to lock the tool into a safe, closed position when the instrument is retracted.

Harness-Mounted Instruments

The concepts of one type of fingertip-mounted minimally invasive surgical instruments, the so-called "harness-mounted" instruments, will now be described in detail with respect to several specific instruments.

Grasper

FIG. 1 shows an exploded view of one type of fingertip-mounted surgical instrument, a grasper 10, that can be used to manipulate or retract tissues, depending on the nature of the teeth in the jaws as described in further detail below. The grasper has three main parts, a harness 20; a retracting/deploying mechanism 30 integrally connected to a "stationary" jaw 31 (which is part of the grasper "tool" in this embodiment); and a moving component 40, which comprises a moving jaw 41 (which is another part of the tool) and an actuator 42. An attachment stud 50 (which is the attachment mechanism in this embodiment) connects harness 20 and retracting/deploying mechanism 30 so that they can rotate with respect to each other. The stationary jaw and retracting/deploying mechanism can be manufactured in one piece, or as two pieces that are rigidly connected. The same holds true for the moving jaw and actuator, which together form moving component 40.

The harness can be made from surgical grade stainless steels or, to decrease weight and manufacturing costs, the harness also can be made from a medical grade, rigid plastic material, e.g., ULTEM® brand polyetherimides, or RADAL® brand polyethersulphones. The harness is preferably a low cost, injection-molded component.

The materials used to manufacture the retracting/deploying mechanism 30, actuator 42, and stationary 31 and moving jaws 41 can vary depending on whether the instrument is best suited as a disposable or a reusable instrument. For reusable instruments, the jaws are made of robust, autoclavable materials such as surgical stainless steels or titanium. For disposable instruments, the jaws can be manufactured of cast alloys, metal injection-molded alloys, or medical grade plastics such as polyethersulphones and polyetherimides, optionally with metal inserts, e.g., for the gripping surfaces or for rigid internal ribs or struts.

Stud 50 is made of high strength surgical stainless steel, plastic, or a light-weight, insulating ceramic.

Figure 11:
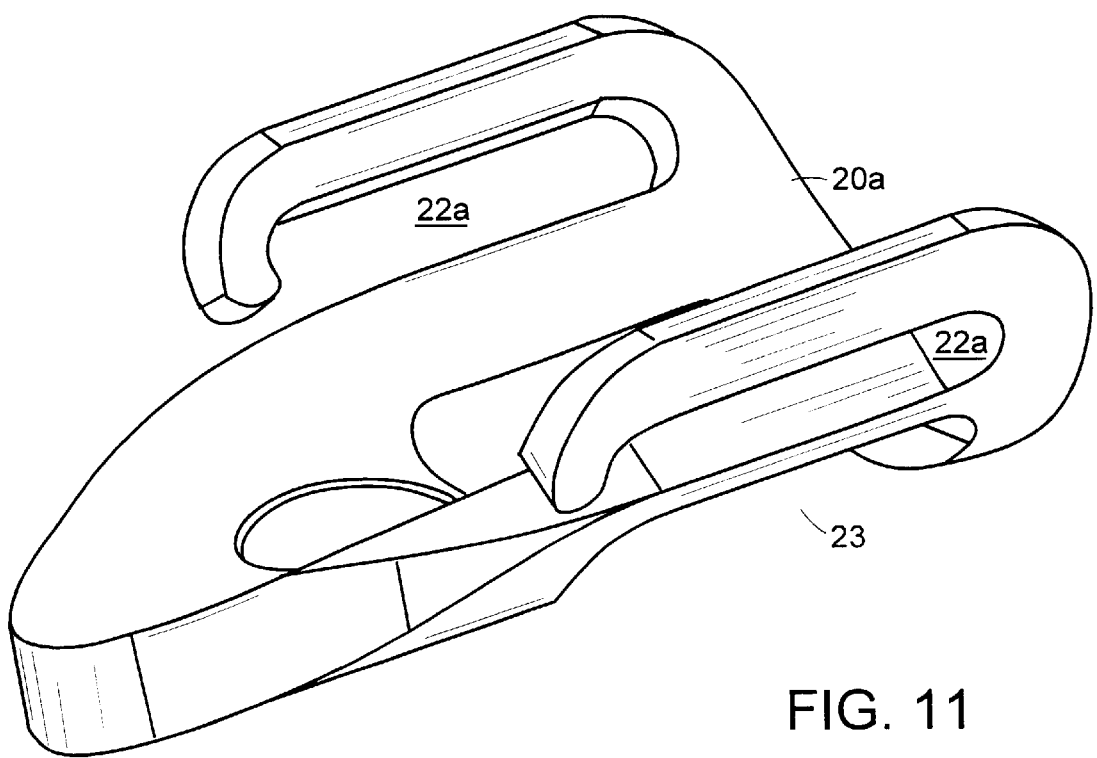
FIG. 11 is an isometric schematic view of an alternative harness for use in fingertip-mounted minimally invasive surgical instruments.

Harness 20 has a pair of cutouts 22 to allow a strap to be passed through the harness and secure the harness to a surgeon's fingertip. For example, the strap could be made of a hook and loop material, e.g., VELCRO®, to loop around and wrap the finger to anchor the harness, and thus the entire instrument, on the fingertip. FIG. 11 shows an alternative harness design in which harness 20a includes cutouts 22a that are open at one end to simplify insertion or removal of a strap or webbing. In other respects this harness 20a is similar to harness 20 shown in FIG. 1. Both harnesses 20 and 20a further include cutout 23 so that as the strap is tightened, the surgeon can feel the strap on the lower portion of the finger to judge whether the harness is properly secured. Cutout 23 also provides easier access for the surgeon's thumb in rotating the retracting/deploying mechanism 30. The harness can also be secured to the finger or gloved finger by adhesive tape, e.g., cloth surgical adhesive tape.

Stationary jaw 31 is so named because it does not move with respect to moving jaw 41, while moving jaw 41 moves with respect to jaw 31. In this embodiment, stationary jaw 31 is an integral part of the retracting/deploying mechanism 30. Thus, both parts move, because mechanism 30 is rotatably attached to harness 20 with attachment stud 50, as described in further detail below. Moving jaw 41 moves because it is rotatably attached to stationary jaw 31 with pivot pin 43.

Stud 50 passes through compression member 55 and a counterbored opening 26 in harness 20, and into hole 32 in retracting/deploying mechanism 30. Compression member 55 is seated on shoulder 53 (FIG. 5) at the bottom of opening 26. Member 55 can be a commercially available O-ring, e.g., made of an elastic material that is suitable for autoclaving (when used in a reusable device), such as polypropylene or silicon, or a commercially available spring, e.g., a helical stainless steel spring. Stud 50 includes a cap 52 and a hollow shaft 54. Shaft 54 can be split at the end opposite the cap as shown in FIG. 1, to allow the shaft to be radially expanded, after insertion into hole 32, to secure the end of shaft 54 in hole 32, e.g., with an insertable pin 56, and, preferably fixed with an adhesive or silver-solder. This arrangement secures retracting/deploying mechanism 30 to harness 20, while allowing rotation of one with respect to the other around central axis 51 of stud 50.

Cap 52 of stud 50 seats almost flush with harness 20 so that it does not protrude substantially above the inner wall of the harness, thereby avoiding any pressure on the surgeon's finger. However, since the inner wall of harness 20 is curved slightly to match the underside of the surgeon's finger, the slight protrusion of cap 52 provides the surgeon with tactile feedback as to whether the flat cap 52 of stud 50 is in its proper position as stud 50 pistons up and down when the tool is moved between the deployed and retracted positions.

Figure 3:
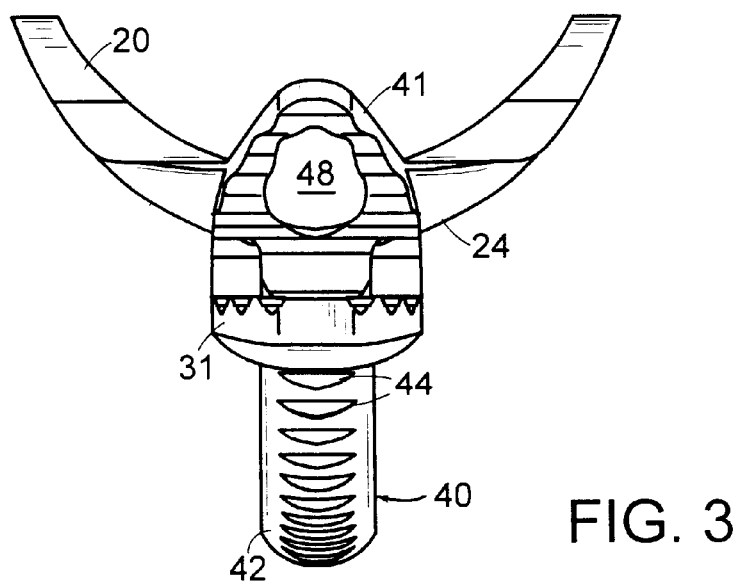
FIG. 3 is a front schematic view of the surgical grasper of FIG. 2.
Figure 4:
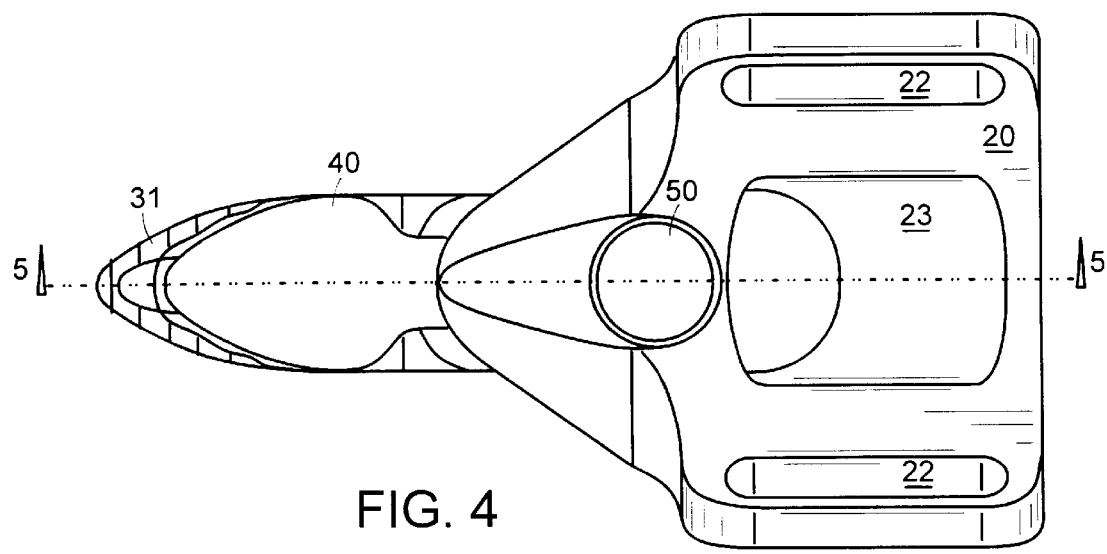
FIG. 4 is a plan schematic view of the surgical grasper of FIG. 2.

The outer surface of harness 20 is curved to form a convex mating surface 24 (as best seen in FIG. 3) that cooperates with a concave mating surface 34 on retracting/deploying mechanism 30. The radii of the curved mating surfaces, which are substantially the same for both surfaces, and the length of shaft 54 of stud 50 are adjusted to compress compression member 55 with cap 52 of stud 50 against shoulder 53 when surfaces 24 and 34 are aligned in parallel, e.g., as shown in FIG. 3, and to provide a maximal compression of ring or spring 55 when surfaces 24 and 34 are rotated out of alignment around axis 51.

Figure 6:
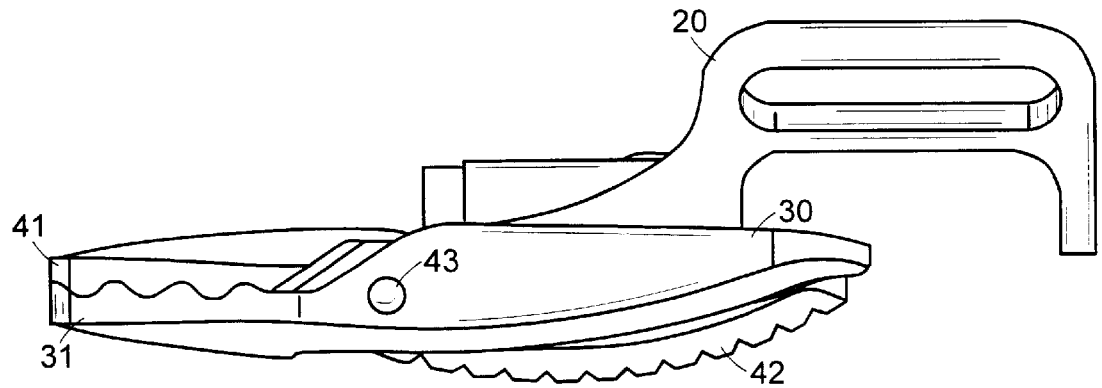
FIG. 6 is a side schematic view of the surgical grasper of FIG. 2 in the deployed position with the jaws closed.
Figure 7:
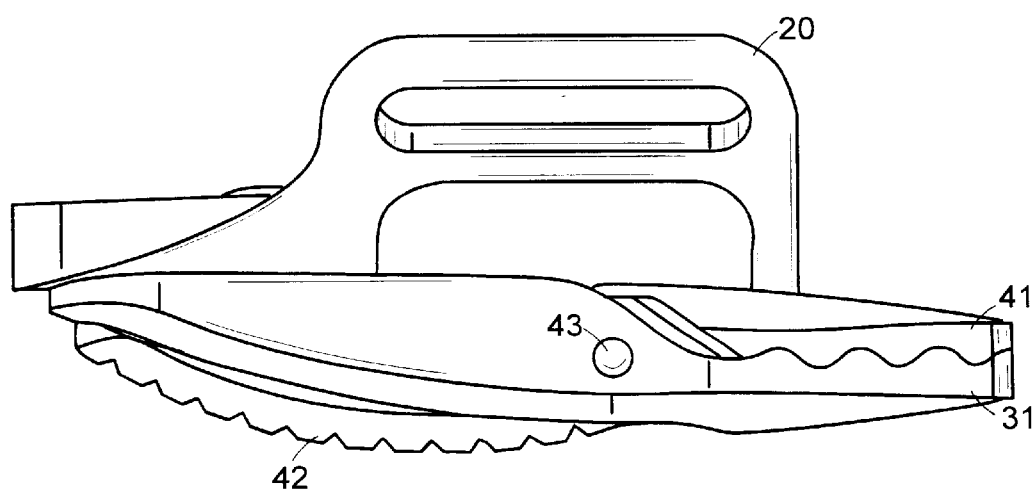
FIG. 7 is a side schematic view of the surgical grasper of FIG. 2 in the retracted position with the jaws closed.

This arrangement allows the surgeon to use his or her thumb to rotate both stationary jaw 31 and moving jaw 41 of the grasper tool from a deployed position, as shown in FIGS. 2 through 6, to a retracted position, as shown in FIG. 7. Compression member 55 provides a constant biasing force that keeps mating surfaces 24 and 34 passively locked in parallel alignment, either in the deployed or retracted positions, until the surgeon applies an actuating force greater than the constant biasing force with his or her thumb to rotate the grasper tool into the desired position.

The additional compression on member 55 serves as an over-center mechanism that biases retracting/deploying mechanism 30 into either one of the locked, deployed or locked, retracted positions.

Figure 2:
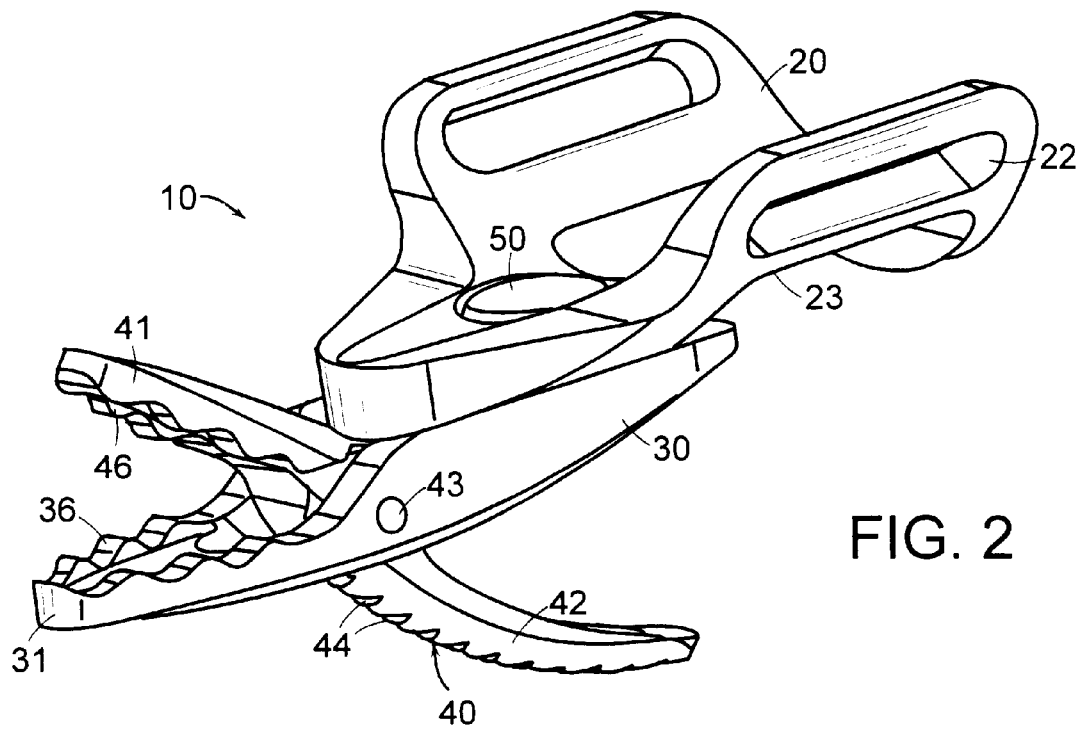
FIG. 2 is an isometric schematic view of the surgical grasper of FIG. 1 in the deployed position with the jaws in the open position.

As shown in FIG. 2, pivot pin 43 secures moving jaw 41 to stationary jaw 31. The pivot pin is made of a high strength steel and is either welded, soldered, press-fit, or orbitally riveted in place. The outer surface of actuator 42 of moving component 40 can include a textured or ribbed surface 44 to provide a better grip and thus more control for the surgeon. Furthermore, actuator 42 is shaped to have two curves that allow the surgeon to comfortably actuate the instrument from a variety of different angles, and to accommodate a variety of different hand sizes. The first curve runs along the longitudinal axis of actuator 42 as shown in, e.g., FIG. 5. The second curve is in the cross-section perpendicular to the longitudinal axis of the actuator, as best seen in FIG. 3.

Gripping surfaces 36 and 46, on stationary jaw 31 and moving jaw 41, respectively, include gripping teeth or gripping and cutting teeth. In the embodiment shown in the figures, the gripping surfaces are designed to manipulate within minimal injury those tissues and organs that are intended to be left in place, and thus include atraumatic, rolled teeth. However, when the gripping surfaces are designed to grip tissues tightly, without regard to injury, e.g., tissues that are to be resected, these teeth are designed as sharp points to provide greater bite or purchase into those tissues.

Gripping surfaces 36 and 46 are formed along the edges of their respective jaws, and include an empty space or fenestration 38 (FIG. 1) and 48 (FIG. 3) milled into the stationary and moving jaws, respectively. This configuration allows the gripping surfaces to exert a more positive grip on tissue. In a disposable device, the jaws can be made of a medical grade plastic, while the gripping surfaces can be made as metal inserts. Alternatively, metal inserts can be molded into the full length of a plastic jaw to provide strength and rigidity, or the entire jaw can be manufactured using metal-injection-molding (MIM) techniques.

As shown in FIG. 5, cavity 33 in retracting/deploying mechanism 30 allows actuator 42 of moving component 40 to be seated flush when the grasper tool is in the closed position as seen in FIGS. 6 and 7. A large portion of the lower section of moving component 40 is actually housed within retracting/deploying mechanism 30 so that the instrument maintains an overall low profile, primarily so that when the instrument is in the retracted position (FIG. 7) it does not impede the surgeon's use of his or her fingertips.

Cavity 33 also provides a space for one end of a return spring 37 which continuously biases moving jaw 41 into an open position. Spring 37 can be a torsion spring, which can be wound around pivot pin 43 and can be made of, e.g., 0.006 to 0.015 inch diameter, high strength stainless steel wire. The spring can be made to have one, two, or three coils, or can be designed as a flat piece of spring steel with no coils. As shown in FIG. 5, the other end of the torsion spring can be seated lengthwise in milled cavity 45 within actuator 42 to provide the maximum return leverage. As an alternative, small magnets can be inserted into the jaws to use magnetic repulsion to keep jaws 31 and 41 biased in an open position.

FIG. 5 also shows a clearance cutout 35 in stationary jaw 31, which allows moving component 40 to be assembled into stationary jaw 31 by passing the moving component down, into, and through the cutout and into place, and then securing the two jaws with pivot pin 43.

The components of the surgical grasper are dimensioned to fit onto a surgeon's fingertip, as shown in FIG. 5. Thus, in a typical configuration, the harness is approximately one inch or less in overall length so that it can fit on the first joint of the finger. The radius used on outer surface of the harness is about a 0.4 inch, and the overall height of the harness is about 0.3 inch. The integral retracting/deploying mechanism 30 and stationary jaw 31 are approximately 1.15 inches long, have an overall height of approximately 0.185 inches, and a width of approximately 0.260 inches. The moving component 40, including actuator 42 and moving jaw 41, is approximately 0.99 or 1.0 inch in overall length, has an overall height of approximately 0.2 inches, and a width comparable to that of the stationary jaw.

Needle Holder

Figure 8:
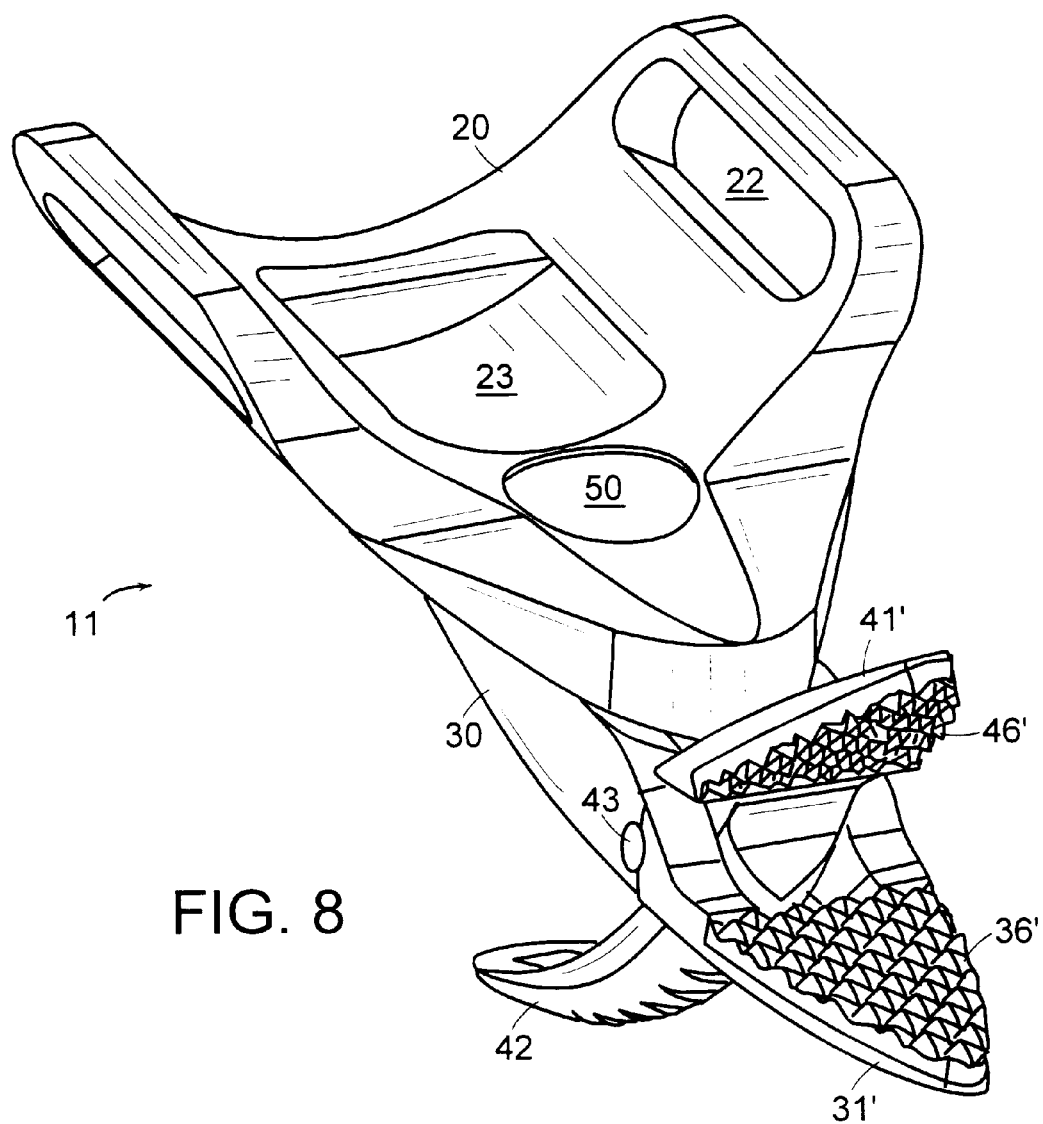
FIG. 8 is an isometric schematic view of a fingertip-mounted minimally invasive suture needle holder.

The suture needle holder is one of several instruments that are similar in general configuration to the grasper described above. As shown in FIG. 8, this instrument 11 includes harness 20, stationary jaw 31', moving jaw 41', and attachment stud 50. The harness and stud are the same as in the grasper described above, and can be manufactured in the same way as well. The overall dimensions are similar to those of the grasper. The retracting/deploying mechanism 30 can also be the same as in the grasper, but is integrally connected to a modified stationary jaw 31'. This jaw 31' can have a somewhat narrower design than jaw 31 in the grasper, but it also can be identical in size. The needle holder also has a spring (not shown) to bias the jaws in the open position, and the moving and stationary jaws are connected by pivot pin 43.

The main difference between the grasper and the needle holder is the nature of the gripping surfaces 36' and 46' of stationary jaw 31' and moving jaw 41', respectively, in the needle holder. These gripping surfaces, e.g., in the form of inserts, must be manufactured of a very hard material such as tungsten carbide steel, and preferably have a textured or knurled surface as shown in FIG. 8. These inserts can be of the same material and manufactured in the same way as the gripping surfaces of commercially available needle holders (e.g., those made by Aesculap A. G., Tuttlingen, Germany).

In another embodiment, the jaws of different instruments can be designed to be identical, and the gripping surfaces can be designed as interchangeable inserts. Thus, the jaws can be designed with fenestrations as in the grasper, and teeth inserts (e.g., as shown in FIGS. 2 and 5) can be replaced with needle holder inserts (as shown in FIG. 8) which cover the fenestrations and provide a wide surface area to hold the needle securely.

As another feature, the needle holder can be manufactured to include a locking mechanism commonly referred to as a ratchet. Such a locking mechanism allows the surgeon to grasp a suture needle and feel the instrument clicking into a ratcheting, locked position that prevents the jaws of the instrument from opening until the surgeon applies pressure to undo the locking ratchet.

Scissors

Figure 9:
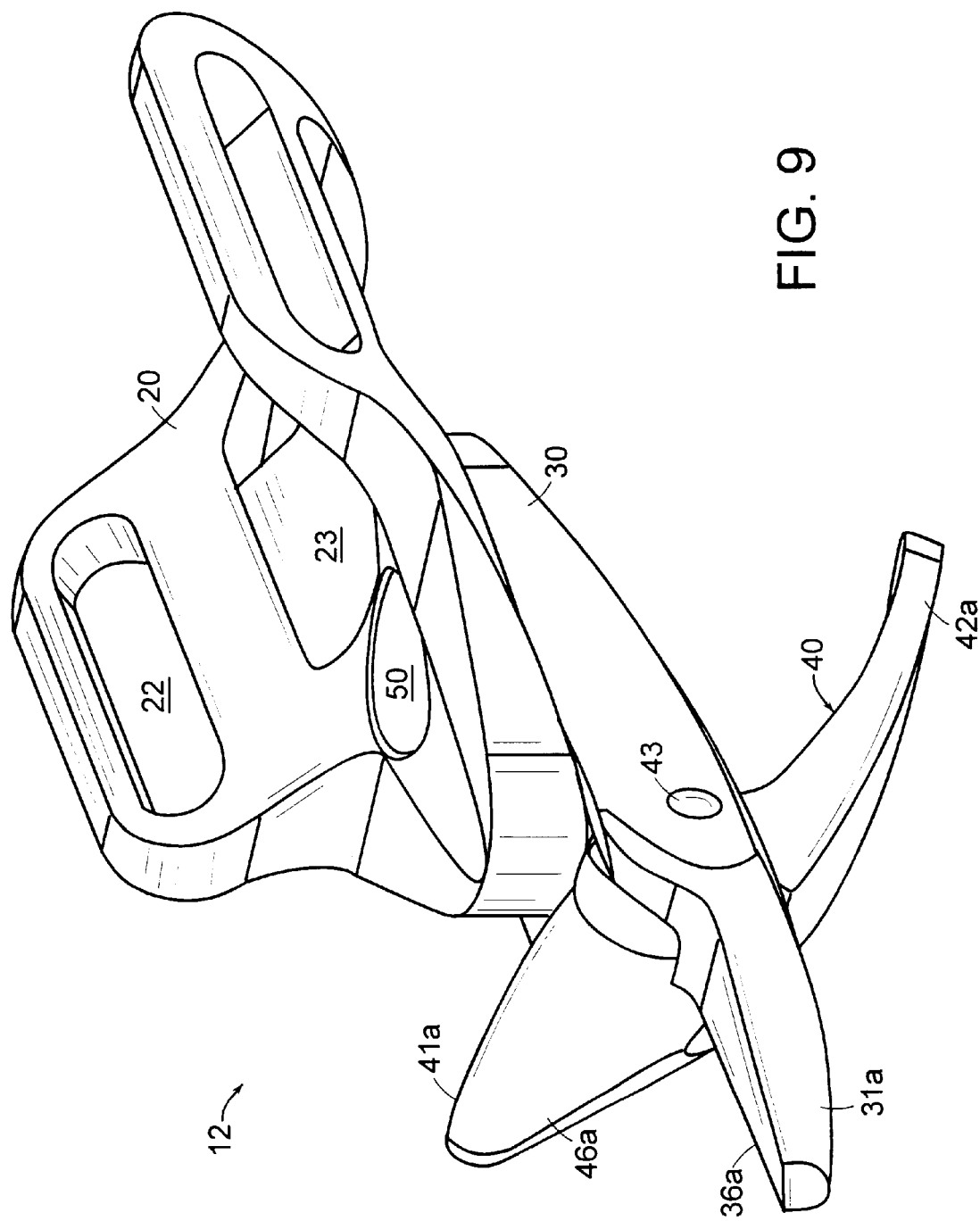
FIG. 9 is an isometric schematic view of a fingertip-mounted minimally invasive scissor.
Figure 10:
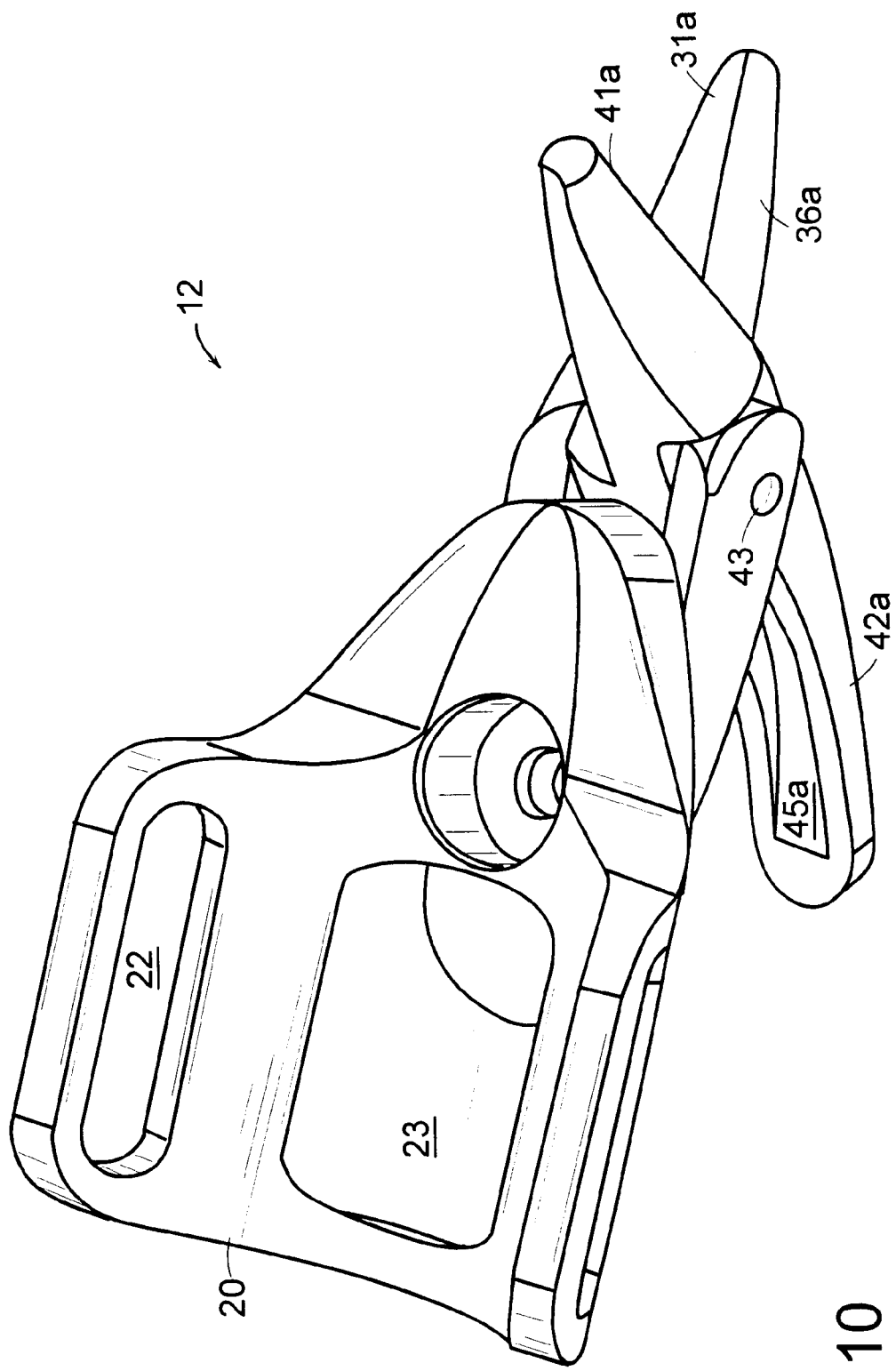
FIG. 10 is an isometric schematic view of the fingertip-mounted minimally invasive scissor of FIG. 9 in a reverse angle view.

Scissors are another example of an instrument that is similar in general configuration to the grasper described above. As shown in FIGS. 9 and 10, this instrument 12 includes a harness 20, stationary jaw 31a, moving jaw 41a, and attachment stud 50. The harness and stud are the same as in the grasper described above, and can be manufactured in the same way as well. The overall dimensions of the scissors are similar to those of the grasper. The retracting/deploying mechanism 30 is also the same as in the grasper, but is integrally connected to a modified stationary jaw 31a. This jaw 31a is modified to include a cutting edge 36a that cooperates in a shearing motion with a cutting edge 46a on moving jaw 41a. The scissors also have a spring (not shown) seated in cutout 45a (FIG. 10) in actuator 42a, to bias the jaws, and their respective blades, in the open position. Moving jaw 41a and stationary jaw 31a are connected by pivot pin 43.

The main difference between the grasper and the scissors is the cutting edges 36a and 46a of stationary jaw 31a and moving jaw 41a, respectively, in the scissors. The jaws are designed so that the cutting edges move past each other in a shearing motion, rather than butt against each other in a clamping motion as in the grasper. These cutting edges, e.g., in the form of inserts, for example if the jaws are made of plastic, must be manufactured of a very hard material such as surgical grade stainless steel or ceramic. These inserts can be of the same material and manufactured in the same way as the blades of commercially available laparoscopic surgical scissors (such as those made by U.S. Surgical Corp., CT).

Tool Cartridge/Holder Instruments

The concept of another type of fingertip-mounted minimally invasive surgical instrument, one having a tool cartridge and a tool cartridge holder, will now be described in detail with respect to several specific instruments.

In general, the cartridge/holder configuration is illustrated in FIG. 12, which shows a hand upon which a tool cartridge/holder assembly 60 is mounted by means of a hook and loop or tape band 61. In this figure, the tool cartridge is a grasper cartridge 70 inserted into holder 62 and opened and closed by actuator 64. The actuator is part of the tool cartridge 70, rather than the holder 62.

Tool Cartridge Holder

As shown in FIG. 13A, holder 62 can be designed as a hollow cylinder having an elliptical or oval cross-section. Holder 62 includes an opening 63 that allows the actuator lever 64 of a tool cartridge to extend out of the holder, and a proximal end 65 into which the tool cartridge can be inserted. The distal end 67 includes two forward tabs or stops 67a and 67b, which prevent the tool cartridge from sliding out of the holder. An oval cross-section allows the tool cartridges to take up as little space as possible, i.e., to provide a low profile, yet provide a wide actuator lever that can be easily and positively felt and operated by the surgeon's thumb. This design also allows the tools to be flat and wide which combines a low profile with an effective tool width.

The holder can also be designed as an open half-cylinder, e.g., a "shell" design, or as a rail onto which a tool cartridge can slide. In any design, the holder must:

(1) be easily and removably attached to a surgeon's finger;
(2) provide a generic base to which different tool cartridges can be easily and interchangeably attached or inserted; and (3) provide access to any actuators attached to the tool cartridge to allow the surgeon to move the tool cartridge from a deployed to a retracted position.

FIG. 13B shows a holder 62 attached to a "wing" or band 61 of adhesive tape (e.g., cloth surgical tape) or hook and loop material that is used to secure the holder to a finger, e.g., a gloved finger. This wing can be attached to the holder by a permanent adhesive, such as a cyanoacrylate or medical grade epoxy, by insert molding when the holder is manufactured, or by ultrasonic welding. The wing 61 also includes a repositionable double-sided adhesive foam tape 68, which is adhered to the wing on one side (facing the holder) and protected by a removable liner 69 on the other side (facing the outside). This foam tape is provided either as two strips, one under each half of the wing 61 (only one is shown in FIG. 13B), or as one strip centered under the holder. This tape allows the surgeon to temporarily position the holder on his or her finger before permanently securing the wing 61 to the finger with the strong surgical adhesive tape that makes up the wing.

Figure 15:
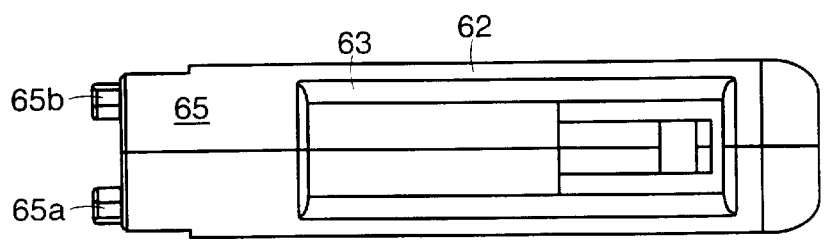
FIGS. 15, 16, and 17 are top, side, and cross-sectional schematic views of a tool cartridge holder.
Figure 16:
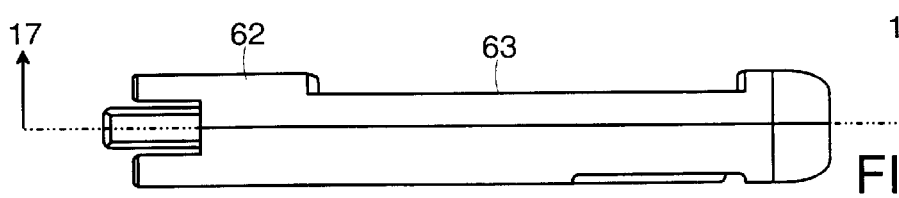
Figure 17:
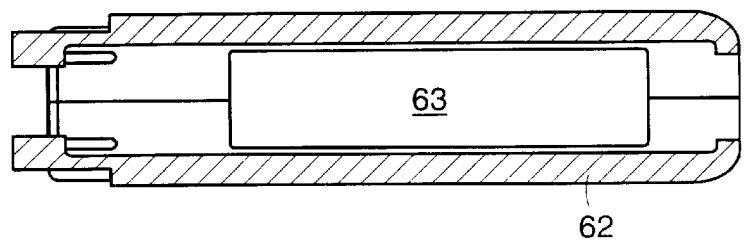

FIG. 14 shows a more detailed view of the proximal end 65 of holder 62. As shown, the proximal end 65 includes two tabs or stops 65a and 65b, which serve to retain the tool cartridge within the holder once the cartridge is slid into the holder. FIGS. 15 through 17 show top, side, and cross-sectional views, respectively of holder 62.

Figure 22:
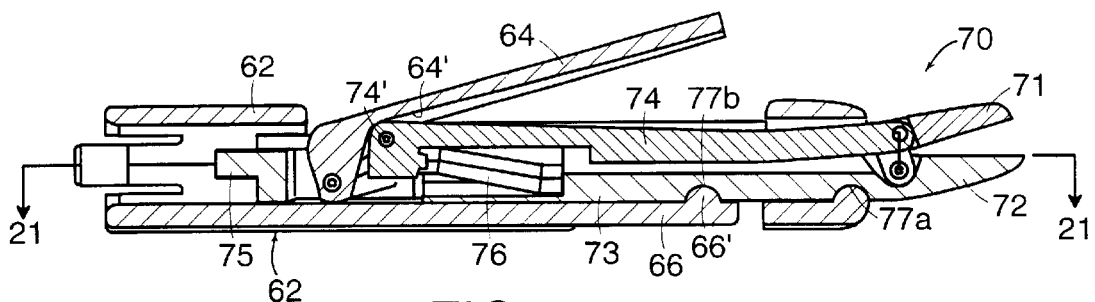
FIG. 22 is a cross-sectional schematic view of the grasper cartridge and holder of FIG. 20A as viewed along line 22—22.

As shown in FIG. 22, holder 62 includes a spring portion 66 that includes a protrusion or detent 66'. This detent 66' fits into distal and proximal detent notches, e.g., 77a and 77b, respectively, in tool cartridge 70, to provide fixed and locked deployed and retracted positions for the tool cartridges within holder 62. The spring portion can be a molded plastic spring, which is created as part of the holder wall, or it can be designed as an insert molded spring, that is initially a separate part which is fixed to the holder wall.

The holder can be made from surgical grade stainless steels or, to decrease weight and manufacturing costs, the holder also can be made from a medical grade, rigid plastic material, e.g., ULTEM® brand polyetherimides, or RADAL® brand polyethersulphones. The holder is preferably a low cost, injection-molded component.

FIGS. 32A and 32B show an extractor tool 100. The extractor tool includes a shaft 101 with a handle 104 at its proximal end and an extractor head 102 at its distal end. The extractor head 102 is configured to contact and grasp the extractor tool interface found at the end of each tool cartridge, e.g., 75 in FIG. 21, to completely remove a tool cartridge, e.g., the grasper cartridge 70, from holder 62. As shown in FIG. 32B, the extractor head 102 includes an opening 103 and a vertical slit 105 that allows extractor tool interfaces to be inserted and grasped by the extractor head 102. In particular, the extractor head 102 is placed on the end of the extractor tool interface, is turned 90 degrees clockwise to lock the extractor tool interface into head 102, and is pulled axially to allow complete removal of the tool cartridge from the holder. The extractor works by rotating and spreading apart the flexible tabs 65a and 65b, in a caming action, which results from the elliptical cross-section of the head 102. Once tabs 65a and 65b are separated, a tool cartridge can be easily removed, whereas the cartridge cannot slip out of the holder with the tabs in their normal position.

In an alternative embodiment, the holder is designed with one or more release buttons that spread the tabs 65a and 65b to allow the tool cartridge to be slid out of the holder without the need for an extractor tool. The release button can be, for example, connected to a tapered or wedge-shaped sliding plastic actuator, which spread the tabs 65*a* and 65*b* apart as the button is slid in the proximal direction.

In one embodiment, a tool cartridge is inserted into the body cavity and into a holder through a protective sleeve 110 (FIG. 35) with the extractor tool. The extractor tool is also used to pull the tool cartridge from the holder directly into the protective sleeve and out of the body cavity. The protective sleeve 110 includes a distal end 114 that contacts the holder (e.g., by being pushed onto the proximal end of the holder), and a proximal end that includes a flange 112, which remains outside of the patient. The sleeve includes an internal portion 116, which provides an oval cross-section. This cross-section allows a tool cartridge to be pulled into the sleeve without rotation that might occur if the inner cross-section of the sleeve were circular. The protective sleeve can have an overall length of about 5 inches, an external diameter of about 10 mm, to fit within standard trocars, and be manufactured from medical grade flexible plastics. The sleeve can also include one or more valves to prevent the escape of insufflation gases.

Grasper

Figure 18B:
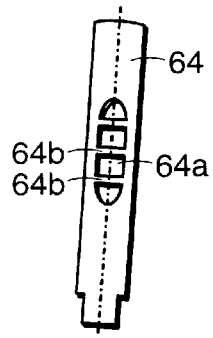
FIG. 18B is a schematic of an alternate actuator configuration.
Figure 18A:
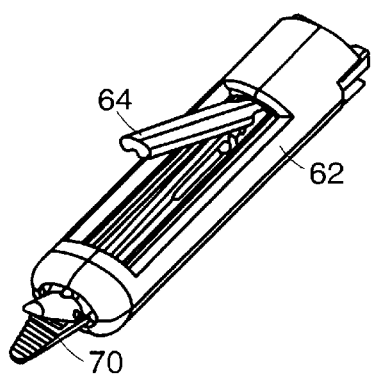
FIG. 18A is an isometric schematic view of a grasper cartridge inserted in a holder and positioned in a deployed and open position.
Figure 19:
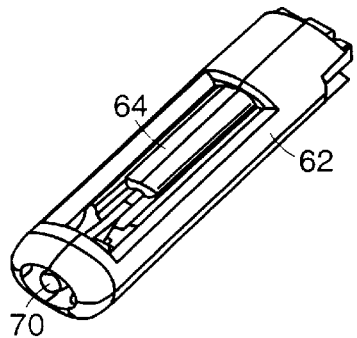
FIG. 19 is an isometric schematic view of the grasper cartridge and holder of FIG. 18, in a retracted and closed position.

FIGS. 18A and 19 show a grasper cartridge 70 inserted into holder 62 and actuated by actuator 64. The grasper can be used to manipulate or retract tissues, depending on the nature of the teeth in the jaws as described herein. FIG. 18A shows the grasper cartridge 70 in an extended and open position. FIG. 19 shows the grasper in a retracted position and actuator 64 in a closed position. FIG. 18B shows an actuator having a textured surface. This actuator 64 includes cutouts 64*a* that form ribs 64*b* to provide the textured surface. The textured surface can have many variations, although the texture should be created by depressions or cutouts in the surface rather than protrusions, to ensure that the actuator will fit within the holder when slid into the closed, retracted position.

Figures 20A, 20B:
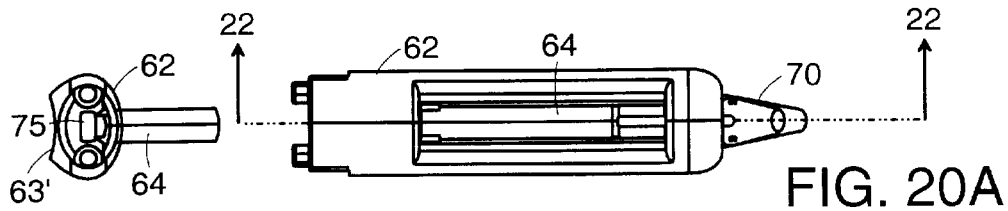
FIG. 20A is a top schematic view of a grasper cartridge in a holder in a deployed and open position.
FIG. 20B is a proximal end view of the grasper cartridge and holder of FIG. 20A.
Figure 21:
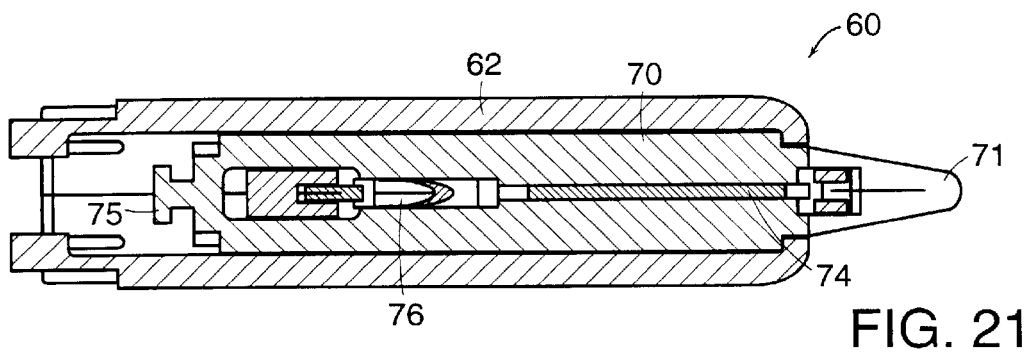
FIG. 21 is a cross-sectional view of the grasper cartridge and holder of FIG. 20A as viewed along line 21—21 in FIG. 22.

The details of the grasper cartridge are best seen in FIGS. 20A through 23. FIGS. 20A and 20B show a top schematic and proximal end view, respectively, of grasper cartridge 70 in an extended or deployed position with actuator 64 in the open position. As shown in FIG. 20B, the surface 63' of the holder 62 that contacts the surgeon's finger is somewhat concave to better match the contour of the finger. FIG. 21 shows a cross-sectional view of the cartridge/holder assembly along line 21—21 in FIG. 22. FIGS. 20A and 21 also show grasper jaw 71 as having a tapered configuration. The jaws can also be designed with a straight and blunt end configuration, a curved and tapered configuration, or other standard grasper configurations.

FIG. 22 shows a detailed cross-section along lines 22—22 in FIG. 20A. As shown in this figure, the grasper cartridge 70 is inserted in holder 62, is extended in a deployed position, and is partially open. Actuator 64 contacts pushrod 74, which in turn is connected to upper jaw 71 of the grasper cartridge 70, by suitable linkages as shown. A cam surface 74' on pushrod 74 contacts actuator 64 on inner surface 64' to provide a leveraged force on upper jaw 71. A similar cam surface configuration can also be used to move jaw 71.

The linkages shown in FIG. 22 use pivot pins. The linkages can also be constructed without pins as described in, e.g., Honkanen, U.S. Pat. No. 4,712,545. Pushrod 74 contacts spring 76 to be biased such that upper jaw 71 tends to remain in an open position. Spring 76 can be a leaf spring, e.g., made of spring steel, a compression coil spring, a separate, pliable plastic material (e.g., SILASTIC®) spring, or a plastic spring molded-in place.

In another embodiment, the actuator 64, pushrod 74, and upper jaw 71 are configured such that downward pressure on actuator 64 causes jaw 71 to open, rather than close as in the grasper cartridge 70. The spring 76 would therefor bias jaw 71 in a closed position. This configuration is useful to construct a blunt dissector tool cartridge for separating tissue layers.

Figure 23:
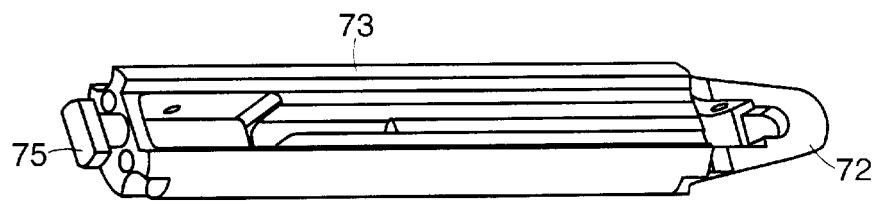
FIG. 23 is an isometric schematic view of a frame for a grasper cartridge.

As best seen in FIG. 23, lower frame 73 of grasper cartridge 70 includes a lower jaw 72 at its distal end and an extractor tool interface 75 at its proximal end. The spring 76, pushrod 74, upper jaw 71, and the actuator 64 are assembled and inserted into hollow frame 73 using standard micro-machining techniques. Once assembled, the entire frame 73 can be slid axially within holder 62. Both jaws 71 and 72 can include gripping surfaces including gripping teeth or gripping and cutting teeth.

Holder 62 includes a spring portion 66 that includes a protrusion or detent 66'. Frame 73 includes distal and proximal detent notches 77A and 77B, respectively. Detent 66' fits into these detent notches to provide fixed and locked deployed and retracted positions for the grasper cartridge 70 within holder 62. The surgeon moves the grasper cartridge 70 within the holder by pushing downwards and backwards on the actuator. First the actuator 64 comes to rest against the pushrod 74, which closes the grasper jaws, and then the surgeon pushes backwards on the actuator until detent 66' clicks into detent notch 77*a*, which causes the entire tool cartridge to slide backwards within the holder 62 and into a locked, retracted position.

The materials used to manufacture the grasper cartridge and all of its parts can vary depending on whether the instrument is best suited as a disposable or a reusable instrument. For reusable instruments, the jaws are made of robust, autoclavable materials such as surgical stainless steels or titanium. For disposable instruments, the jaws can be manufactured of cast alloys, metal injection-molded alloys, or medical grade plastics such as polyethersulphones and polyetherimides, optionally with metal inserts, e.g., for the gripping surfaces or for rigid internal pushrod or actuator.

The components of the surgical grasper are dimensioned to fit onto a surgeon's fingertip, as shown in FIG. 12. Thus, in a typical configuration, the holder is approximately one and one half inch or less in overall length so that it can fit within the first two joints of the finger. The long diameter of the oval shape of the holder is about a 0.375 inch, and the overall height of the holder can be about 0.3 inch. The tool cartridge has an oval cross-section and has a long diameter of about 0.236 inches, and the height can be about 0.157 inches. The cartridge is about 1.2 inches long. The overall wide and flat cross-section provides a low profile with adequate strength for the tools and provides a relatively wide surface to provide excellent finger-feel for the surgeon.

Needle Holder

A suture needle holder can be designed and manufactured in much the same way as the grasper described above. The appearance of the needle holder would be essentially the same as the grasper, with the only significant difference being the nature of the gripping surfaces of the lower and upper jaws in the needle holder. These gripping surfaces, e.g., in the form of inserts, are manufactured of a very hard material such as tungsten carbide steel, and preferably have a textured or knurled surface, e.g., as shown in FIG. 8 for the harness-mounted needle holder. These inserts can be made of the same material and manufactured in the same way as the gripping surfaces of commercially available needle holders (e.g., those made by Aesculap A. G., Tuttlingen, Germany). The overall dimensions are similar to those of the grasper.

Scalpel

Figures 24A, 24B:
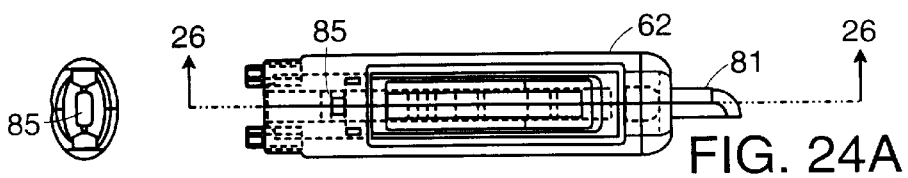
FIG. 24A is a top schematic view of a scalpel cartridge in a holder.
FIG. 24B is a proximal end view of the scalpel cartridge and holder of FIG. 24A.
Figure 25:
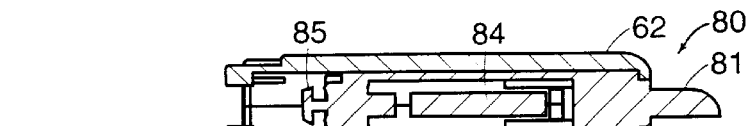
FIG. 25 is a cross-sectional view of the scalpel cartridge and holder of FIG. 24A, as viewed along line 25—25 in FIG. 27.

FIGS. 24A through 29 depict a scalpel cartridge 80 inserted in housing 62. FIGS. 24A and 24B show a top and proximal end view, respectively. As shown in FIG. 25, scalpel cartridge 80 includes a scalpel blade 81 at its distal end, and an extractor tool interface 85 at its proximal end. The scalpel cartridge 80 differs from the grasper cartridge 70 in that it does not have a lever as the actuator to open and close the tool, but instead includes a thumb switch 84 as the retracting/deploying mechanism. Thumb switch 84 can be knurled, ribbed, or fitted with protruding tabs to provide a more positive grip for the surgeon.

Figures 26A, 26B:
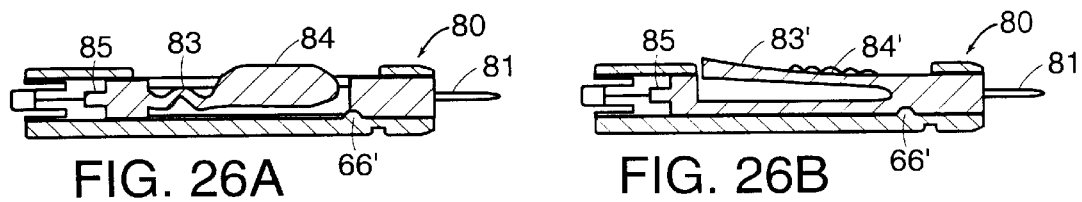
FIGS. 26A and 26B are cross-sectional views of the scalpel cartridge and holder of FIG. 24A, as viewed along line 26—26 in FIG. 24A.
Figure 27:
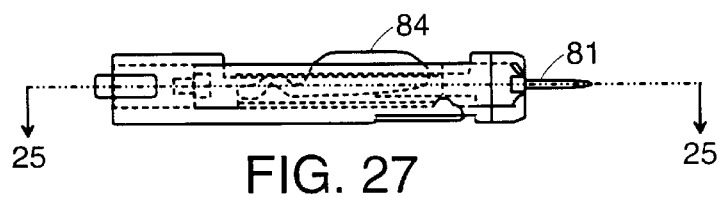
FIG. 27 is a side schematic view of the scalpel cartridge and holder of FIG. 24A.
Figure 28A:
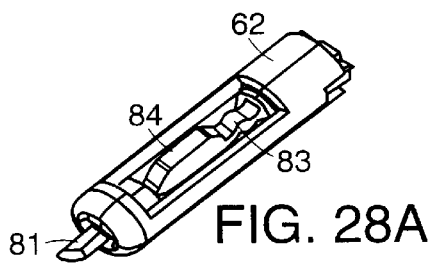
FIGS. 28A and 28B are isometric schematic views of a scalpel cartridge in a holder in deployed and retracted positions, respectively.
Figure 28B:
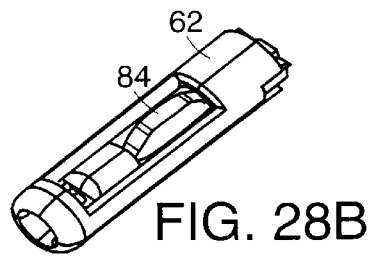
Figure 29A:
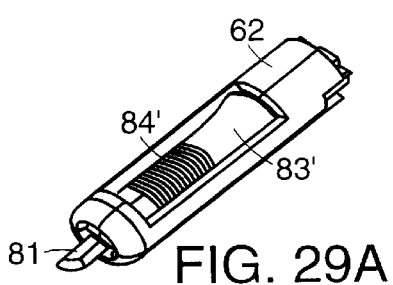
FIGS. 29A and 29B are isometric schematic views of an alternative embodiment of a scalpel cartridge and holder in deployed and retracted positions, respectively.
Figure 29B:
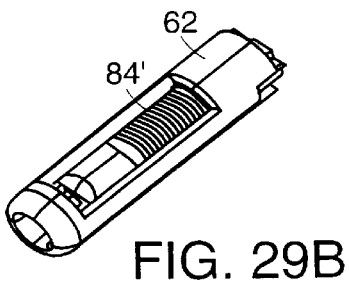

As shown in FIGS. 26A, thumb switch 84 is connected to tool cartridge 80 by means of a molded spring 83. In the deployed position (FIG. 28A), switch 84 is pressed down and back to retract the scalpel 81 into a retracted position (FIG. 28B). FIG. 26B shows an alternative embodiment of the scalpel cartridge, which includes a ribbed or knurled thumb switch 84' on the surface of a spring plate 83'. In this embodiment, the surgeon presses down on thumb switch 84' to push down spring plate 83', which allows the scalpel cartridge 80 to be retracted (FIG. 29B). When the scalpel is in the retracted position, the surgeon can move thumb switch 84' forwards a sufficient distance until spring plate 83', which is biased in an outward direction, automatically extends out of opening 63 in holder 62 to snap into place to provide a locked, deployed position (FIG. 29A).

As best shown in FIG. 30, scalpel cartridge 80 includes a distal detent notch 87 at its distal end and a proximal detent notch 86. These two detent notches cooperate with detent 66' in holder 62 to provide deployed and retracted fixed and locked positions. The complete cartridge 80 is shown in three-quarter view in FIG. 31.

Camera

As shown in FIGS. 36A and 36B, the tool cartridge can be configured as a charge-coupled device (CCD) camera 120 using standard components and miniaturization techniques, e.g., as used in manufacturing endoscopes. The surface of the cartridge includes depressions or cutouts 124 to provide a gripping surface to allow the camera to be slid within a holder. The camera cartridge 120 includes a lens assembly 122 and light sources or light transmitters 123. The cartridge includes a CCD camera assembly 128, e.g., a Panasonic CCD (No. GP-KD262HS). The CCD camera is connected by a plug assembly 130 and multiple wires 132 to a cable 124 that extends from the cartridge 120 and runs along the surgeon's hand and arm, e.g., to a monitor outside the patient.

The camera and light source can be supplied with electricity through cable 124 from a power source located outside the patient, or from a battery located within cartridge 120 (see, e.g., Oz, U.S. Pat. No. 5,079,629). Alternatively, light can be transmitted to the light transmitters 123 through a fiber optic cable located within cable 124 from a light source outside the patient. Signals from the CCD camera can be transmitted to a monitor through cable 124 or by an antenna (not shown), e.g., as described in Oz, U.S. Pat. No. 5,079,629.

Scissors

Scissors are similar in general configuration to the grasper described above with respect to FIGS. 18A to 23. As shown in FIGS. 37A and 37B, this tool cartridge 140 includes a frame 143, a stationary jaw 142, a moving jaw 141, a pushrod 144, a spring 146, an extractor tool interface 145, and an actuator 64. These parts, including the pushrod and actuator, are essentially the same as in the grasper described above, and can be manufactured in the same way as well.

Again, the cam surface 144' of pushrod 144 contacts inner surface 64' of actuator 64. The overall dimensions of the scissors are similar to those of the grasper. The only significant difference between the grasper and the scissors is in the design of the jaws.

In the scissors, the lower jaw 142 on the cartridge frame 143 is modified to include a cutting edge 142' that cooperates in a shearing motion with a cutting edge 141' on upper, moving jaw 141. The scissors also have a spring 146 to bias the jaws, and their respective cutting edges, in the open position. The cutting edges, e.g., in the form of inserts, for example if the jaws are made of plastic, must be manufactured of a very hard material such as surgical grade stainless steel or ceramic. These inserts can be of the same material and manufactured in the same way as the blades of commercially available laparoscopic surgical scissors (such as those made by U.S. Surgical Corp., CT).

Clip Applier

A clip applier is used to attach metal or plastic clips to tissues, such as blood vessels. This tool can be adapted to both the harness-mounted instruments and the holder/cartridge assembly. The design is similar to that described above for the grasper, but has a somewhat different jaw configuration designed to apply a clip rather than grasp or resect tissue. The clip applier requires a different spring mechanism than the one used in the grasper described above. The spring can be mounted in the same way as in the grasper, but must be arranged to bias the jaws into an open, but not fully open position, so that the spring returns the jaws to this position if opened to the full extent, i.e., when loading the jaws with a clip, and when closing the jaws, i.e., when applying the clip.

Electrocauterizing Instruments

Any of the surgical instruments described above, when made of an electrically conducting material, can be adapted to provide an electrocautery feature.

For example, any tool including two jaws can be easily adapted to provide bipolar electrocautery. Such an adaptation requires that the harness or holder be made of an insulating material such as plastic, or be electrically insulated from the retracting/deploying mechanism or tool cartridge, e.g., coated with a standard electrosurgical insulation. Further, the retracting/deploying mechanism and the tool or tool cartridge must be insulated as well, except for the cauterizing tip of the tool.

As an alternative, only one of the jaws of the tool could be used for monopolar electrocautery, and the other jaw could be made of an insulating material such as plastic. The plastic coating would cover the entire length of the instrument with a very small bare portion at the most distal tip of the instrument. Because the instruments of the invention are mounted directly on the surgeon's fingertips, the bipolar cautery embodiment is the preferred method of electrocautery.

To adapt a particular instrument, e.g., the harness-mounted grasper described above, for bipolar electrocautery, moving component 40 and moving jaw 41 are electrically insulated from retracting/deploying mechanism 30 and stationary jaw 31 with ceramic disks or wafers around pivot pin 43 (the pivot pin is preferably coated with an insulating material, e.g., ceramic), and harness 20 also is made of a plastic or ceramic material to insulate the surgeon. Furthermore, attachment stud 50 is preferably made of, or coated with, an insulating material, e.g., a ceramic. Electrically conductive fittings are attached, e.g., soldered or machined in place, on both the moving component 40 and the retracting/deploying mechanism 30. Wires are connected to these fittings at one of their ends, and are connected at their other ends to a controllable power source.

During bipolar operation, current flows from one jaw, e.g., moving jaw 41, to the other jaw, e.g., stationary jaw 31, through the target tissue to be cauterized between the two jaws. During monopolar operation, current flows from one scalpel, or other instrument, into the target tissue, and through the patient to a ground. In both embodiments, the majority of the surfaces of the one or two jaws are preferably insulated so that the current flow can be controlled.

As another example, FIG. 33 shows that the tool cartridge/holder embodiment can also be adapted as an electrocautery tool. For example, FIG. 33 shows a spoon blade electro-cautery tool cartridge 90. Cartridge 90 includes a spoon blade 91 at its distal end and an extractor tool interface 95 at its proximal end. As shown in FIG. 33, electrocautery spoon cartridge 90 includes distal and proximal detent notches 97 and 96, respectively, to provide positive locking deployed and retracted positions once inserted into a holder 62. The spoon blade 91 is deployed or retracted by a thumb grip 94 connected to the cartridge 90 by means of a molded spring 93. The spoon electrocautery cartridge 90 is connected to a power source (not shown) by means of a conducting wire 98.

The flow of electricity to the tool or tool cartridge can be controlled using standard techniques, e.g., a foot pedal or switch connected to the power generator.

Fluid Conduits

Any of the instruments described above can be outfitted with fluid conduits for both irrigation and aspiration using standard components and methods. Commercially available fluid tubing sets can be connected to the instruments, e.g., to the tool harness or holder, or to the tool cartridge, and run along the surgeons finger and arm, and attached to standard pumping mechanisms (such as those made by Smith & Nephew Dyonics, MA and Davol, RI). Aspiration conduits are connected to standard vacuum ports.

Control buttons for actuating and stopping irrigation and suction can be located on flexible appendages attached to the proximal end of the harness and arranged on or along the surgeon's finger or fingers so that the surgeon can press the buttons with the thumb. Alternatively, these functions could be controlled by a foot pedal or switch that controls the flow of fluids or vacuum. These foot pedals come as standard equipment with most fluid and vacuum pumps.

Manufacture of Fingertip-Mounted Minimally Invasive Surgical Instruments

The surgical instruments can be constructed using known manufacturing techniques and materials. For example, the mount, e.g., harness or holder, can be injection molded, and can be the same size and shape in different types of instruments; thus the harness and holder are the most likely candidates for mass production. In addition, the harness and holder are likely to be disposable. For reusable instruments, such as, for example, the stationary and moving jaws of the tools, and the cartridge and retracting/deploying mechanism, are preferably machined from a surgical stainless steel or other metal using standard machine practices. Certain tools or tool cartridges are preferably reusable, such as, for example, the graspers and needle holders. On the other hand, tools that require sharp blades or that are used for electrocautery are preferably disposable with metal inserts molded in place (insert molded) or ultrasonically welded in place.

As an example, the gripping surfaces and fenestrations described for the grasper can be created by electron discharge machining (EDM). In particular, the teeth of the gripping surfaces can be created by wire EDM, and the fenestrations can be made using ram or sinker EDM. The cutouts and cavities, e.g., for the spring, can be created by similar EDM procedures.

Instruments with tools such as scalpels or scissors that include blades or edges that must be kept extremely sharp, as well as tools used for electrocautery, where the degree of burning or charring would make the instruments difficult to clean, are preferably produced as disposable instruments. These disposable instruments are constructed of plastics with metal inserts molded or ultrasonically adhered in place. Instruments that are intended to be used as graspers and soft tissue dissectors can be made to be reusable and sterilizable. The sterilizable instruments are preferably constructed of all stainless steel, or of autoclavable plastic with stainless steel tool tips. Alternatively, both the disposable and reusable instruments can be manufactured using metal-injection-molding techniques.

Methods of Use

The fingertip-mounted instruments are best used in hand-assisted minimally invasive surgical procedures within the abdomen or pelvis, such as are currently performed by laparoscopic surgery. Other sites within the body can be accessed as well. In addition, the new instruments can be used in traditional, open surgery as well, in place of traditional surgical instruments such as forceps, scalpels, and scissors.

In a minimally invasive setting, diagnostic aspects of any procedure are carried out using standard laparoscopic techniques with a small incision. Once an accurate diagnosis is made, the surgeon enlarges the incision to 2 to 3 inches, depending on the size of his or her hand and wrist, and prepares the patient cavity, e.g., by insufflating the cavity with a gas. The surgeon then inserts a standard laparoscope or other device to enable constant visualization of the interior of the cavity during surgery.

The surgeon then secures a mount (holder or harness) on his or her index or middle finger, and can secure up to three additional mounts onto the three other fingers (one instrument on each finger). As an alternative, one or more harness-mounted instruments or holders can be pre-mounted, e.g., by adhesive, metal, or plastic staples, or other means, on the fingertips of a sterilized glove, e.g., of a cloth mesh or weave material. Initially, the instruments are all mounted in the retracted position. In the case of the tool cartridge/holder assemblies, the holders are mounted empty (or with a tool cartridge already inserted), and tool cartridges are interchangeably inserted and extracted from the holder with the extractor tool as described herein. A surgeon can test the position of the holder by inserting a tool cartridge into holder, temporarily mounting the holder to his or her gloved finger with repositionable tape, deploying the tool to see whether the tool extends beyond the fingertip, and then fixing the holder's position with the surgical tape wing.

In one scenario, the tool cartridges described herein are exchanged outside the body cavity. In an alternative scenario, the tool cartridges can be loaded into a magazine that is inserted into the body cavity by means of standard laparoscopic surgical techniques and trocars. The tool cartridges can be moved from the magazine to the holder and vice versa, by means of a long extractor tool, and inserted into and removed from the tool holder connected to the surgeon's finger, all within the body cavity. Such manipulations of standard laparoscopic tools, which are manipulated and actuated by long shafts that extend out of the body cavity, are described in Dannan, U.S. Pat. No. 5,441,059.

Once the patient cavity is ready for surgery, the surgeon inserts his or her hand equipped with the one to four different instruments through the incision. The surgeon then makes full use of his hand in manipulating tissues, performing blunt dissection, running bowels, probing for tumors, etc. When the need arises for resection, dissection, ligation, etc. by instrument, the surgeon deploys the appropriate instrument with a simple movement of his or her the thumb, whereby the required tool is moved into the locked, deployed position. The instruments can be individually or multiply deployed and retracted as needed. All instruments are preferably retracted before the surgeon removes his or her hand from the cavity.

Other Embodiments

It is to be understood that while the invention has been described in conjunction with the detailed description thereof, that the foregoing description is intended to illustrate and not limit the scope of the invention, which is defined by the scope of the appended claims.

Other aspects, advantages, and modifications are within the scope of the following claims.

What is claimed is:

1. A fingertip-mounted minimally invasive surgical instrument comprising,
   a mount for securing the instrument to a fingertip;
   a retracting/deploying mechanism operably connected to the mount; and
   a tool connected to the retracting/deploying mechanism, wherein the retracting/deploying mechanism is arranged to permit the tool to be moved into a retracted position relative to the mount to expose the fingertip, and into a deployed position relative to the mount for use of the tool.

2. An instrument of claim 1, wherein the mount is a harness that is permanently connected to the retracting/deploying mechanism.

3. An instrument of claim 1, wherein the mount is a holder and is operably connected to the retracting/deploying mechanism by being attached temporarily to a tool cartridge.

4. An instrument of claim 2, further comprising an attachment mechanism that rotatably connects the harness to the retracting/deploying mechanism.

5. An instrument of claim 4, wherein the attachment mechanism comprises an attachment stud and a compression member arranged to secure the retracting/deploying mechanism to the harness and to enable the retracting/deploying mechanism to rotate from a deployed position to a retracted position.

6. An instrument of claim 5, wherein the harness comprises a convex outer surface that mates with a concave surface of the retracting/deploying mechanism.

7. An instrument of claim 1, wherein the tool comprises a stationary jaw connected to the retracting/deploying mechanism, and a moving jaw rigidly fixed to an actuator.

8. An instrument of claim 7, wherein the actuator has a curved cross-section, and is curved along its longitudinal axis.

9. An instrument of claim 7, further comprising a spring arranged to bias the moving jaw in an open position with respect to the stationary jaw.

10. An instrument of claim 7, wherein a portion of the retracting/deploying mechanism is hollowed out to house the actuator when the tool is in a closed position.

11. An instrument of claim 1, wherein the mount comprises openings for insertion of a strap to secure the mount to a finger.

12. An instrument of claim 1, wherein said tool is a grasper, scissors, a scalpel, a clip applier, a needle holder, a camera, or an electrocautery blade.

13. A fingertip-mounted minimally invasive surgical instrument assembly comprising,
    a tool cartridge holder for securing the instrument to a fingertip, and
    an elongate tool cartridge comprising a frame and a tool connected to a distal end of the frame,
    wherein the frame is configured to be movably attached to the holder, and the frame and holder are configured such that the frame and the attached tool can move between a retracted position and a deployed position relative to the holder.

14. An assembly of claim 13, wherein the holder comprises a hollow, cylindrical housing and the tool cartridge is attached to the holder by being inserted into the housing, and wherein the tool is sheathed within the housing when the tool cartridge is moved into a retracted position, and extends outside of the housing when the tool cartridge is moved into a deployed position.

15. An assembly of claim 13, wherein the holder comprises a detent that engages a first notch on the tool cartridge frame to provide a locked, deployed position.

16. An assembly of claim 15, wherein the tool cartridge frame further comprises a second notch, and wherein the detent engages the second notch to provide a locked, retracted position.

17. An assembly of claim 13, wherein the tool cartiridge comprises a stationary jaw, and a moving jaw connected to an actuator.

18. An assembly of claim 13, wherein the tool is a grasper, scissors, a scalpel, a clip applier, a needle holder, a camera, or an electrocautery blade.

19. An assembly of claim 13, wherein the holder comprises stops at distal and proximal ends of the holder to temporarily prevent the tool cartridge from being removed from the holder absent manipulation by the surgeon.

20. An assembly of claim 13, wherein the tool cartridge further comprises a retracting/deploying mechanism, and the holder comprises an opening to provide access to the retracting/deploying mechanism.

21. An instrument of claim 1, wherein the mount comprises an adhesive band to secure the mount to a fingertip.

22. An assembly of claim 13, wherein the holder comprises an adhesive band to secure the holder to a fingertip.

23. An assembly of claim 13, further comprising an extractor tool configured to engage an extractor interface on a proximal end of the tool cartridge frame.

24. An assembly of claim 23, further comprising a protective sleeve, said sleeve comprising an elongate, hollow cylinder configured to contact the holder and allow the tool cartridge to be removed with the extractor tool through the lumen of the sleeve.

25. A method of performing a minimally invasive surgical procedure in a patient, said method comprising,
    creating in the patient an incision sized to fit a hand;
    securing an instrument of claim 1 to a fingertip of the hand;
    inserting the hand including the instrument into the patient; and
    performing the surgical procedure using the instrument.

26. A method of claim 25, further comprising securing an additional instrument onto another of the fingers prior to inserting the hand into the patient.

27. A method of claim 25, wherein the tool of the instrument is moved into a deployed position prior to performing the surgical procedure, and into a retracted position after performing the surgical procedure, without removing the hand from within the patient.

28. A method of claim 25, wherein the tool of the instrument is moved into a retracted position to enable the finger to be used to manipulate tissue in the patient, without removing the hand from within the patient.

29. An instrument of claim 1, further comprising fittings to attach fluid aspiration or irrigation conduits to the mount.

30. An instrument of claim 1, further comprising fittings to attach electrical wiring to provide the instrument with an electrocautery capability.

\* \* \* \* \*